(12) United States Patent
McMorris et al.

(10) Patent No.: US 7,655,695 B2
(45) Date of Patent: Feb. 2, 2010

(54) ILLUDIN ANALOGS USEFUL AS ANTICANCER AGENTS

(75) Inventors: Trevor C. McMorris, La Jolla, CA (US); Michael J. Kelner, La Jolla, CA (US)

(73) Assignee: The Regents of The University of California, Oakland, CA (US)

( * ) Notice: Subject to any disclaimer, the term of this patent is extended or adjusted under 35 U.S.C. 154(b) by 0 days.

(21) Appl. No.: 11/997,432

(22) PCT Filed: Aug. 3, 2006

(86) PCT No.: PCT/US2006/030439

§ 371 (c)(1),
(2), (4) Date: Jul. 7, 2008

(87) PCT Pub. No.: WO2007/019308

PCT Pub. Date: Feb. 15, 2007

(65) Prior Publication Data

US 2008/0306147 A1    Dec. 11, 2008

Related U.S. Application Data

(60) Provisional application No. 60/705,017, filed on Aug. 3, 2005.

(51) Int. Cl.
| | |
|---|---|
| A61K 31/27 | (2006.01) |
| A61K 31/17 | (2006.01) |
| A61K 31/13 | (2006.01) |
| C07C 271/18 | (2006.01) |
| C07C 271/22 | (2006.01) |
| C07C 239/14 | (2006.01) |
| C07C 239/18 | (2006.01) |
| C07C 275/22 | (2006.01) |
| C07C 275/24 | (2006.01) |
| C07C 335/10 | (2006.01) |

(52) U.S. Cl. ............... 514/479; 514/480; 514/645; 514/580; 514/588; 514/595; 560/115; 560/119; 564/17; 564/56; 564/57; 564/300

(58) Field of Classification Search .............. 514/479, 514/480, 645, 580, 588, 595; 560/115, 119; 564/17, 56, 57, 300
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,612,302 A | 9/1986 | Szabo et al. | |
| 4,684,620 A | 8/1987 | Hruby et al. | |
| 4,820,508 A | 4/1989 | Wortzman | |
| 4,853,371 A | 8/1989 | Coy et al. | |
| 4,938,949 A | 7/1990 | Borch et al. | |
| 4,992,478 A | 2/1991 | Geria | |
| 5,164,526 A | 11/1992 | Macher | |
| 5,387,578 A | 2/1995 | Angelucci et al. | |
| 5,439,936 A | 8/1995 | Kelner et al. | |
| 5,439,942 A | 8/1995 | Kelner et al. | |
| 5,523,490 A | 6/1996 | Kelner et al. | |
| 5,563,176 A | 10/1996 | Kelner et al. | |
| 5,723,632 A | 3/1998 | McMorris | |
| 5,932,553 A | 8/1999 | McMorris et al. | |
| 6,025,328 A | 2/2000 | McMorris et al. | |
| 6,069,283 A | 5/2000 | McMorris et al. | |
| 6,235,789 B1 * | 5/2001 | Ohkawa et al. | 514/630 |
| 6,323,181 B1 | 11/2001 | McMorris et al. | |
| 6,380,403 B1 | 4/2002 | McMorris et al. | |
| 6,548,679 B1 | 4/2003 | McMorris et al. | |
| 6,639,105 B2 | 10/2003 | McMorris et al. | |
| 6,855,696 B2 | 2/2005 | McMorris et al. | |
| 6,908,918 B2 | 6/2005 | McMorris et al. | |
| 6,987,193 B2 | 1/2006 | McMorris et al. | |
| 7,141,603 B2 | 11/2006 | McMorris et al. | |
| 7,329,759 B2 | 2/2008 | McMorris et al. | |
| 2005/0250675 A1 | 11/2005 | McMorris et al. | |
| 2006/0194744 A1 | 8/2006 | McMorris et al. | |
| 2007/0072790 A1 | 3/2007 | McMorris et al. | |
| 2008/0306013 A1 | 12/2008 | McMorris et al. | |

FOREIGN PATENT DOCUMENTS

EP    1056704 B1    5/2003

(Continued)

OTHER PUBLICATIONS

"PCT Application No. PCT/US2006/030439, International Search Report mailed May 18, 2007", 4 pgs.
.."Written Opinion of the International Searching Authority for Application No. PCT/US2006/030439, date mailed May 18, 2007", 7 pgs.
"U.S. Appl. No. 09/641,191, Non Final Office Action mailed Apr. 23, 2001", 11 pgs.
"U.S. Appl. No. 09/641,191, Non Final Office Action mailed May 3, 2002", 8 pgs.
"U.S. Appl. No. 09/641,191, Notice of Allowance mailed Sep. 19, 2002", 10 pgs.
"U.S. Appl. No. 09/641,191, Response filed Oct. 23, 2001 to Non Final Office Action mailed Apr. 23, 2001", 7 pgs.
"U.S. Appl. No. 09/641,191, Response filed Aug. 5, 2002 to Non Final Office Action mailed May 3, 2002", 11 pgs.
"U.S. Appl. No. 09/641,191, Preliminary Amendment mailed Aug. 17, 2000", 1 pgs.

(Continued)

Primary Examiner—Peter G O'Sullivan
(74) Attorney, Agent, or Firm—Schwegman, Lundberg & Woessner, P.A.

(57) ABSTRACT

Acylfulvene analogs, which inhibit tumor growth, especially solid tumor growth, and which have an adequate therapeutic index to be effective for in vivo treatment are provided herein. The compounds described herein are useful as anti-neoplastic agents, i.e., to inhibit tumor cell growth in vitro or in vivo, in mammalian hosts, such as humans or animals, e.g., domestic animals, and are effective against solid tumors, hematologic malignancies and multi-drug resistant cancers/tumors. The present compounds can be used alone or they can be used in combination with one or more anti-cancer or anti-tumor agents.

42 Claims, 5 Drawing Sheets

FOREIGN PATENT DOCUMENTS

| | | |
|---|---|---|
| EP | 0915819 B1 | 5/2004 |
| HU | 208115 B | 8/1993 |
| HU | 72450 | 4/1996 |
| JP | 62-234040 A | 1/1987 |
| JP | 5-503077 A | 5/1993 |
| JP | 8-506812 T | 7/1996 |
| JP | 3-908270 B2 | 4/2007 |
| WO | WO-91/04741 A1 | 4/1991 |
| WO | WO-91/04754 A2 | 4/1991 |
| WO | WO-94/18151 A1 | 8/1994 |
| WO | WO-94/25013 | 11/1994 |
| WO | WO-96/34005 A1 | 10/1996 |
| WO | WO-97/03995 A1 | 2/1997 |
| WO | WO-98/03458 A1 | 1/1998 |
| WO | WO-98/005669 A1 | 2/1998 |

OTHER PUBLICATIONS

"U.S. Appl. No. 10/413,449, Non Final Office Action mailed Jun. 22, 2004", 5 pgs.
"U.S. Appl. No. 10/413,449, Notice of Allowance mailed Oct. 21, 2004", 5 pgs.
"U.S. Appl. No. 10/413,449, Response filed Sep. 24, 2004 to Non Final Office Action mailed Jun. 22, 2004", 11 pgs.
"U.S. Appl. No. 10/413,449, Preliminary Amendment mailed Apr. 14, 2003", 3 pgs.
"U.S. Appl. No. 11/151,013, Non-Final Office Action mailed Jan. 24, 2006", 4 pgs.
"U.S. Appl. No. 11/151,013, Notice of Allowance mailed Jun. 21, 2006", 6 pgs.
"U.S. Appl. No. 11/151,013, Response filed May 24, 2006 to Non Final Office Action mailed Jan. 24, 2006", 7 pgs.
"U.S. Appl. No. 11/151,013, Preliminary Amendment mailed Jun. 15, 2005", 5 pgs.
"U.S. Appl. No. 11/600,375, Response filed Jun. 13, 2008 to Restriction Requirement mailed May 13, 2008", 11 pgs.
"U.S. Appl. No. 11/600,375, Preliminary Amendment mailed Nov. 16, 2006", 12 pgs.
"U.S. Appl. No. 11/600,375, Response filed Jun. 29, 2009 to Final Office Action mailed Apr. 30, 2009", 11 pgs.
"U.S. Appl. No. 11/600,375, Response filed Feb. 16, 2009 to Non Final Office Action mailed Aug. 14, 2008", 11 pgs.
"U.S. Appl. No. 11/600,375, Non-Final Office Action mailed Aug. 14, 2008", 15 pgs.
"U.S. Appl. No.11/600,375, Final Office Action mailed Apr. 30, 2009", 6 pgs.
"U.S. Appl. No. 11/600,375, Notice of Allowance mailed Jul. 31, 2009", 4 Pgs.
"U.S. Appl. No. 11/955,247, Non-Final Office Action mailed Jun. 11, 2009", 12 pgs.
"U.S. Appl. No. 11/312,236, Notice of Allowance mailed Sep. 13, 2007", 7 pgs.
"Canadian Application Serial No. 2,321,149, Office Action mailed Aug. 26, 2008", 4 pgs.
"Canadian Application Serial No. 2,321,149, Response filed Feb. 24, 09 to Office Action mailed Aug. 26, 2008", 46 pgs.
"Canadian Application Serial No. 2,262,648, Official Action mailed Jul. 30, 2008", 2 pgs.
"Canadian Application Serial No. 2,262,648, Official Action mailed Oct. 30, 2006", 3 pgs.
"Canadian Application Serial No. 2,262,648, Official Action mailed Apr. 30, 2009", 2 pgs.
Canadian Application Serial No. 2,262,648, Response filed Jan. 30, 2009 to Official Action mailed Jul. 30, 2008, 14 pgs.
"Canadian Application Serial No. 2,262,648, Response filed Apr. 30, 2007 to Official Action mailed Oct. 30, 2006", 3 pgs.
"European Application Serial No. 04012220, European Search Report mailed Jul. 15, 2004", 5 pgs.
"Japanese Application Serial No. 10-507009, Notice of Reasons for Rejection mailed Dec. 4, 2007", (w/ English Translation), 8 pgs.
"Japanese Application Serial No. 10-507009, Response filed Jan. 4, 2008 to Notice of Reasons for Rejection mailed Dec. 4, 2007", (w/ English Translation of Amended Claims), 20 pgs.
"Japanese Application Serial No. 10-508128, Notice of Reasons for Rejection mailed 8-26- 2008", (w/ English Translation), 11 pgs.
"Japanese Application Serial No. 10-508128, Notice of Reasons for Rejection mailed Jan. 22, 2008", (w/ English Translation), 8 pgs.
"Japanese Application Serial No. 10-508128, Response filed Nov. 25, 2008 to Office Action mailed Aug. 26, 2008" (w/ English Translation of Amended Claims), 15 pgs.
"Japanese Application Serial No. 10-508128, Response filed Jul. 9, 2008 to Notice of Reasons for Rejection mailed Jan. 22, 2008", (w/ English Translation of Amended Claims), 6 pgs.
"Japanese Application Serial No. 2000-532383, Notice of Reasons for Rejection mailed Mar. 10, 2009", (w/ English Translation), 12 pgs.
"Norwegian Application Serial No. 20004162, Office Action mailed Jul. 22, 2009" (w/ English Translation), 4 pgs.
"Norwegian Application Serial No. 20004162, Office Action mailed Jan. 20, 2009" (w/ English Translation), 2 pgs.
"Norwegian Application Serial No. 20004162, Office Action mailed Sep. 11, 2007", (w/ English Translation), 4 pgs.
"Norwegian Application Serial No. 20004162, Response filed Apr. 22, 2009 to Office Action mailed Jan. 20, 2009", (w/ English Translation of Claims), 66 pgs.
"Norwegian Application Serial No. 20004162, Response filed May 9, 2008 to Office Action mailed Sep. 11, 2007", (w/ English Translation of Claims), 31 pgs.
Anchel, M., et al., "The Biogenesis of Illudins S and M in Clitocybe Illudens", Phytochemistiv, 9(11), (Nov., 1970), 2339-2343.
Anchel, Marjorie, et al., "Antibiotic Substances From Basidiomycetes. VII. Clitocybe Illudens", *Proceedings of the National Academy of Sciences*, 36 (5), (1950), 300-305.
Arap, Wadih, et al., "Cancer Treatment by Targeted Drug Delivery to Tumor Vasculature in a Mouse Model", *Science*, 279, (Jan. 16, 1998), 377-380.
Brandsteterova, E., et al., "HPLC Analysis of Novel Anti-Cancer Agents-Illudens and Their Analogs", *Journal of Liquid Chromatography*, 16(1), (1993), 115-125.
Brandsteterova, E., et al., "HPLC Determination of a New Anticancer Agent (Acylfulvene) in Serum", *Neoplasma*, 39 (6), (1992), 369-373.
Burres, N. S., et al., "Antitumor Activity and Mechanism of Action of the Novel Marine Natural Products Mycalamide-A and -B and Onnamide", *Cancer Research*, 49, (Jun. 1989), 2935-2940.
Curtis, E. A., et al., "An Efficient Dipolar-Cycloaddition Route to the Pterosin Family of Sesquiterpenes", *Tetrahedron Letters*, 36(12), (Mar., 1995), 1989-1992.
Dillman, R. O., et al., "Athymic Mouse Model of a Human T-Cell Tumor" *Cancer Research*, 45, (Nov. 1985), 5632-5636.
Fassina, G., "Oriented Immobilization of Peptide Ligands on Solid Supports", *J Chromatogr.*,591, Abstract Only, Obtained from Chemical Abstracts, Accession No. 1992:174737, (1992), 1 p.
French, A. L., et al., "Poisoning with the North American Jack 0' Lantern Mushroom", *Clinical Toxicology* 26, 1988 ,81-88.
Giovanella, B. C., et al., "Correlation Between Response to Chemotherapy of Human Tumors in Patients and in Nude Mice", *Cancer*, 52, (1983), 1146-1152.
Giovanella, B. C., et al., "DNA Topoisomerase I-Targeted Chemotherapy of Human Colon Cancer in Xenografts", *Science*, 246 (Nov. 24, 1989), 1046-1048.
Goldin, A., et al., "Current Results of the Screening Program at the Division of Cancer treatment, National Cancer Institute", *Euro. J. Cancer*, 17, (1981), 129-142.
Goldin, A., et al., "Historical Development and Current Strategy of the National Cancer Institute Drug Development Program", *In: Methods in Cancer Research, vol. XVI: Cancer Drug Development, Part A*, Chapter V, Academic Press, Inc., New York, (1979), 165-245.
Greene, T. W., "Chapters 4, 5 and 6," *Protective Groups in Organic Synthesis*, John Wiley & Sons, Inc., New York, (1981), 114-217.
Hanson, J. R., et al., "Studies in terpenoid biosynthesis. Part XV. Biosynthesis of the sesquiterpenoid illudin M", *Journal of the Chemical Society*, Perkin Transactions I, (1976), 876-880.

Hara, M., et al., "6-Deoxyilludin M, a New Antitumor Antibiotic: Fermentation, Isolation and Structural Identification", *The Journal of Antibiotics*, 40, (Nov., 1987), 1643-1646.

Harttig, U., et al., "Leaianafulvene, a Sesquiterpenoid Fulvene Derivative from Cultures of Mycena Leaiana", *Phytochemistry*, 29 (12), 1990, 3942-3944.

Hirono, I., et al., "Reproduction of Acute Bracken Poisoning in a Calf with Ptaquiloside, a Bracken Constituent", *The Veterinary Record*, 115 (15), (Oct., 1984), 375-378.

Inoue, K., et al., "Antitumor Efficacy of Seventeen Anticancer Drugs in Human Breast Cancer Xenograft (MX-1) Transplanted in Nude Mice", *Cancer Chemother. Pharamacol.*, 10, (1983), 182-186.

Ito, R. K., et al., "Biocompatible Substances with Thromboresistance", U.S. Patent No. 5,019,393, Abstract Only, Obtained from Chemical Abstracts, Accession No. 1991:499399, (May 28, 1991), 1 p.

Kawato, Y., et al., "Antitumor Activity of a Camptothecin Derivative, Cpt-11, Against Human Tumor Xenografts in Nude Mice", *Cancer Chemother. Pharmacol.*, 28, (1991), 192-198.

Kelner, M. J., et al., "In Vitro and in Vivo Studies on the Anticancer Activity of Dehydroilluden M", Anticancer Research 15, (1995), 873-878.

Kelner, M. J., et al., "Nonresponsiveness of the Metastatic Human Lung Carcinoma MV522 Xenograft to Conventional Anticancer Agents", *Anticancer Research*, 15, (1995),867-872.

Kelner, M. J., et al., "Preclinical Evaluation of Illudens as Anticancer Agents", *Cancer Research*, 47 (12), (1987), 3186-3189.

Kelner, M. J., et al., "Preclinical Evaluation of Illudens as Anticancer Agents: Basis for Selective Cytotoxicity", *J. Natl. Cancer Inst.*, 82 (19), (1987), 1562-1565.

Kinder, Jr., Frederick R., et al., "Total Synthesis of (±)-Illudin M", *J. Org. Chem.*, 59 (23), Jul. 13, 1994 ,6965-6967.

Lu, Jianliang, et al., "An expeditious synthesis of the potent antitumor agent, (+)- hydroxymethylacylfulvene using an allenic Paulson-Khand type cycloaddition", *Proceedings of the 217th ACS National Meeting*, (Abstract 038),(Mar. 21-25, 1999), 2 pgs.

Matsumoto, T., et al., "An Alternative Synthesis of Illudin M", *Tetrahedron Letters*, (No. 14), (Mar., 1970), 1171-1174.

Matsumoto, T., et al., "Synthesis of Illudin S", *Tetrahedron Letters*, 23, (May, 1971), 1171-1174.

McMorris, T. C., et al., "(Hydroxymethyl) Acyfulvene: An Illuden Derivative with Superior Antitumor Properties", *Journal of Natural Products*, 59 (9), (Sep., 1996), 896-899.

McMorris, T. C, et al., "(Hydroxymethyl)Acyfulvene: an Illuden Derivative with Superior Antitumor Properties", *Chemical Abstracts*, 125 (Abstract No. 125:196032d), (Oct 7, 1996), p. 1251.

McMorris, T. C., et al., "Acylfulvenes, a New Class of Potent Antitumor Agents", *Experientia*, 52 (1), (1996), 75-80.

McMorris, T. C., et al., "Design and Synthesis of Antitumor Acylfulvenes", *The Journal of Organic Chemistry*, 62 (9), (1997), 3015-3018.

McMorris, T. C., et al., "Fungal Metabolites. The Structures of the Novel Sesquiterpenoids Illudin -S and -M", *Journal of the American Chemical Society*, 87(7), (1965), 1594-1600.

McMorris, T. C., et al., "Metabolism of Antitumor Acylfulvene by Rat Liver Cytosol", *Biochemical Pharmacology*, 57, (1999), 83-88.

McMorris, T. C., et al., "On the Mechanism of Toxicity of Illudens: The Role of Glutathione", *Chemical Research Toxicology*, 3 (6), (Nov./Dec., 1990), 574-579.

McMorris, T. C., et al., "Reaction of Antitumor Hydroxymethylacylfulvene (HMAF) with Thiols", *Tetrahedron*, 53 (43), 1997, 14579-14590.

McMorris, T. C., et al., "Structure and reactivity of Illudens", *Tetrahedron*, 45(17), (1989), 5433-5440.

McMorris, T. C., et al., "Structure-Activity Relationships of Illudens: Analogs with Improved Therapeutic Index", *Journal of Organic Chemistry*, 57(25), (Dec. 4, 1992), 6876-6883.

McMorris, T. C, et al., "Total Synthesis of Hydroxymethylacylfulvene, an Antitumor Derivative of Illudin S", *Chemical Communications*, (1997), 315-316.

McMorris, T. C., et al., "An Acetal Derivative of Illudin S with Improved Antitumor Activity", *Tetrahedron letters*, 38 (10) , (1997), 1697-1698.

Muratami, T., et al., "Weitere Inhaltsstoffe au *Pteris oshimensis* Hieron", *Chemical and Pharmaceutical Bulletin*, 23, (1975), 1890-1892.

Ng, Kam-Mui, et al., "An Efficient Synthesis of Pterosin C and Other Pterosins", *Canadian Journal of Chemistry*, 62 (10), (Oct., 1984), 1945-1953.

Padwa, A., et al., "An approach toward the Illudin family of sesquiterpenes using the tandem cyclization-cycloaddition reaction of rhodium carbenoids", *J. Org. Chem.. American Chemical Society, Easton US*, 62 (5) , (Mar. 7, 1997), 1317-1325.

Padwa, A., et al., "Generation and Cycloaddition behavior of spirocyclic carbonyl ylides. Application to the synthesis of the Pterosin Family of Sequiterpenes", *J. Org. Chem. American Chemical Society. Easton US*, 61 (1) , (Jan. 12, 1996), 73-81.

Padwa, A., et al., "Synthetic studies toward Illudins and Ptaguilosin. A Highly Convergent approach via the dipolar cycloaddition of carbonyl ylides", *The Journal of the American Chemical Society*, 116, (1994), 2667-2668.

Schabel, F. M., et al., "Testing Therapeutic Hypotheses in Mice and Man: Observations on the Therapeutic Activity Against Advanced Solid Tumors of Mice Treated with Anticancer Drugs that Have Demonstrated or Potential Clinical Utility for Treatment of Advanced Solid Tumors of Man", *In: Methods in Cancer Research, vol. XVII: Cancer Drug Development Part B*, Chapter 1, Academic Press, Inc., (1979), p. 3-50.

Sengupta, P., et al., "Isolation and Structure of Wallichoside a Novel Pteroside from Pteris Wallichiana", *Phytochemistry*, 15(6), (1975), 995-998.

Shimomura, O., "The Role of Superoxide Dismutase in Regulating the Light Emission of Luminescent Fungi", *The Journal of Experimental Botany*, 43 (2561, (Nov., 1992), 1519-1525.

Shinozawa, S., et al., "The Antitumor Effect of Illudin S (Lampterol) Entrapped in Liposome for Mice Inolculated with Ehrlich Ascites Tumor Cells", *Chemical Abstracts*, 90 (25), (Abstract No. 197682m), (Jun. 18, 1979), p. 48.

Steel, G. G., et al., "The Response to Chemotherapy of a Variety of Human Tumor Xenografts", *Br. J. Cancer*, 47, (1983), 001-013.

Tanaka, K., et al., "Metabolism by Rat Liver Cytosol of Illuden S, a Toxic Substance of *Lampteromyces Japonicus*. II. Characterization of Illuden S-Metabolizing Enzyme", *Xenobiotica*, 22 (1) (1992), 33-39.

Tanaka, K., et al., "Michael-type addition of illudin S, a toxic substance from *Lampteromyces japonicus* with Cysteine and Cysteine-containing peptides in vitro", *Chem. Pharm. Bull.*, vol. 44, 1996 , 273-279.

Tanaka, N., et al., "Chemical and Chemotaxonomical Studies of Ferns. XXXIX. Chemical Studies on the Constituents of Pteris belie Tagawa and Pteridium aquilinum subsp. wightianum (Wall) Shich", *Chemical and Pharmaceutical Bulletin*, 30(10), (1982), 3640-3646.

Varki, N. M., et al., "Cloned Low Metastic Variants from Human Lung Carcinoma Metastases", *Anticancer Research*, 10, (1990), 637-644.

Venditti, J. M., et al., "Current NCI preclinical antitumor screening in vivo: results of tumor panel screening, 1976-1982, and future directions", *Advances in Pharmacology and Chemotherapy*,20, (1984), 1-20.

Venditti, J. M., "The National Cancer Institute antitumor drug discovery program, current and future perspectives: a commentary", *Cancer Treatment Reports*, 67 (9), (Sep., 1983),767-772.

Walser, J., et al., "Mode of Action of Illuden S", *Antimicrobial Agents and Chemotherapy*, 3 (3), (Mar., 1973), 357-363.

Weinreb, S. M., "Fulvenes Derived from Illuden S", *Tetrahedron Letters*, 38, (Sep., 1971), 3489-3491.

Wij, Meena, et al., "Indanone Derivatives from *Pteris wallichiana*", *Indian Journal of Chemistry*, 15B(1), (1976), 16-17.

Wilbraham, "Amino Acids, Peptides and Proteins", *In: Organic and Biological Chemistry* , (1984), p. 222.

Wolff, M. E. *Burgers Medicinal Chemistry and Drug Discovery*, Fifth Edition (vol. 1: Principles and Practice), John Wiley & Sons, Inc., New York, N. Y., (1995), 785-786.

* cited by examiner

ILLUDIN ANALOGS USEFUL AS ANTICANCER AGENTS

RELATED APPLICATIONS

This application is a U.S. National Stage Filing under 35 U.S.C. 371 from International Patent Application Ser. No. PCT/US2006/030439, filed Aug. 3, 2006, and published on Feb. 15, 2007 as WO 2007/019308 A2 and republished as WO 2007/019308 A3, which claims the priority benefit of U.S. Provisional Application Ser. No. 60/705,017 filed Aug. 3, 2005, the contents of each publication and application are incorporated herein by reference.

BACKGROUND OF THE INVENTION

Malignant neoplasia is the second most common cause of death in the United States behind cardiovascular disease (*National Vital Statistics Reports.* 2005, 53, 7). New cancer chemotherapeutic agents and methods of care combined with early detection and treatment have been largely responsible for decreases in both the overall incidence of cancer and death rates from all cancers combined (Jemal, A. et al., *Cancer.* 2004, 101, 4). There remain many cancer patients for whom no or minimally effective therapy exists. Furthermore, cancers that are initially responsive to current therapies may become resistant and increasingly difficult or impossible to treat. There is an unmet need for novel chemotherapeutics with greater efficacy or safety, either as monotherapy or in combination with other chemotherapeutic agents, and such agents with the potential to overcome drug resistance in cancer cells.

The mushroom *Omphalotus illudens* is a source of the highly toxic sesquiterpenes illudin S and M (1, 2). (See, e.g., McMorris, T. C. et al., *J. Am. Chem. Soc.* 1963, 85, 831).

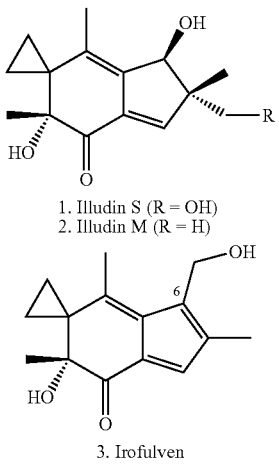

1. Illudin S (R = OH)
2. Illudin M (R = H)

3. Irofulven

These compounds were tested by the National Cancer Institute and were found to possess anti-tumor activity but with a poor therapeutic index. (See, e.g., Kelner, M. J. et al., *Cancer Research* 1987, 47, 3186). However, certain derivatives of these compounds have shown greatly improved efficacy as anti-tumor agents with a better safety profile. In particular, the derivative irofulven (3) (McMorris, T. C. et al., *J. Nat. Prod.* 1996, 59, 896) has been extensively investigated and is currently in phase II clinical trials against ovarian, prostate and gastrointestinal cancers, both as a monotherapy (Cvitkovic E. et al., *J. Clin. Oncol.* 2004, 22, 4766; and Falcon-Lizaraso, S. et al., *J. Clin. Oncol.* 2004, 22, 333) and in combination with well known anticancer agents. In fact, irofulven has demonstrated clinical activity with an acceptable safety profile in hormone-refractory prostate cancer (Senzer N. et al., *Am. J. Clin. Oncol.* 2005, 28, 36). Most relevant to clinical applications, irofulven activity is independent of common resistance mechanisms such as the multidrug resistance phenotype, anti-apoptotic bcl-2 over expression, as well as p53 and $p21^{wafl/cip1}$ mutations (Kelner M. J. et al., *Cancer Res.,* 1995, 55, 4936; Poindessous V. et al., *Clin Cancer Res.* 2003, 9, 2817; and Herzig M. C. et al., *Biochem Pharmacol.* 2003, 65, 503).

There exists a continuing need for chemotherapeutic agents that inhibit solid (e.g., tumor) and non-solid, such as hematologic, cancer cell growth and which have an adequate therapeutic index to be effective for in vivo treatment.

SUMMARY OF THE INVENTION

One embodiment provides acylfulvene analogs which inhibit cancer cell growth, especially solid tumor growth, and which have an adequate therapeutic index to be effective for in vivo treatment. In one embodiment, the compounds are acylfulvene analogues which have been modified with hydroxyurea or a derivative thereof. The compounds have the general formula (I):

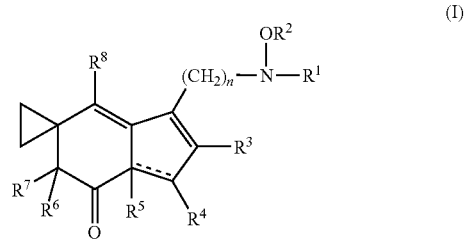

wherein
$R^1$ is —C(=$X^1$)—$X^2$—($R^9$) or H;
$X^1$ is O, or S;
$X^2$ is —O—, —S—, or —N($R^{10}$)—;
$R^2$ is hydrogen, —C(=O)($C_1$-$C_6$)alkyl, —C(=O)($C_1$-$C_6$)alkyl($C_6$-$C_{10}$)aryl, —C(=O)($C_6$-$C_{10}$)aryl, or ($C_1$-$C_6$)alkyl;
$R^3$ is hydrogen, or ($C_1$-$C_6$)alkyl;
$R^4$ is hydrogen, —SCH$_2$CO$_2$($C_1$-$C_6$)alkyl, —O—($C_6$-$C_{10}$)aryl, or —S—($C_6$-$C_{10}$)aryl; where aryl is optionally substituted with halo, OH or ($C_1$-$C_4$)alkyl;
$R^5$ is hydrogen, OH, or absent;
$R^6$ is hydrogen, or ($C_1$-$C_6$)alkyl; and
$R^7$ is OH or Si(($C_1$-$C_4$)alkyl)$_3$; or
$R^6$ and $R^7$ together are ethylenedioxy;
$R^8$ is ($C_1$-$C_6$)alkyl; optionally substituted with OH or halo;
$R^9$ is hydrogen, ($C_1$-$C_6$)alkyl, —($C_1$-$C_4$)alkyl($C_6$-$C_{10}$)aryl, or —($C_6$-$C_{10}$)aryl; or —($C_1$-$C_4$)alkyl($C_6$-$C_{10}$)heteroaryl, or —($C_6$-$C_{10}$)heteroaryl;
$R^{10}$ is hydrogen, —OH, or ($C_1$-$C_6$)alkyl;
n is 1, 2, 3, 4, 5, or 6; and
the bond represented by — is optionally present or absent; and pharmaceutically acceptable salts thereof.

In one embodiment, the compounds of formula (I) are useful as anti-neoplastic agents, i.e., to inhibit cancer cell growth in vitro or in vivo, in mammalian hosts, such as humans or animals, e.g., domestic animals, and are effective against solid tumors, hematologic malignancies and multidrug resistant tumors. In one embodiment, the compounds described herein can be used in a method for treating cancer, alone or in combination with one or more additional anti-cancer or anti-tumor agents.

Another embodiment provides pharmaceutical compositions, such as a solution, or pharmaceutical unit dosage forms, comprising an effective anti-neoplastic amount of one or more of the present acylfulvene analogs in combination with a pharmaceutically acceptable carrier.

In one embodiment, the compounds described herein can be used in combination with other active agents, e.g., one or more anti-cancer agents. Such combinations are selected based on the condition to be treated, cross-reactivities of ingredients and pharmacodynamic properties of the combination. It is also possible to combine the compounds described herein with one or more other active agents in a unitary dosage form for simultaneous or sequential administration to a patient. The combination therapy can be administered as a simultaneous or sequential regimen. When administered sequentially, the combination may be administered in two or more administrations.

The combination therapy can provide "synergy" and/or a "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

In one embodiment the anti-cancer agents or anti-tumor agents can be administered in conjunction with a chemotherapeutic agent, such as an alkylating agent or an anti-androgen or anti-estrogen, monoclonal antibody, anti-angiogenic, radiation and/or other anti-cancer therapy.

Examples of chemotherapeutic agents include, but are not limited to, (trans, trans, trans)-bis-μ-(hexane-1,6-diamine)-μ-[diamine-platinum(II)]-bis[diamine(chloro)platinum (II)] tetrachloride, 1-(11-dodecylamino-10-hydroxyundecyl)-3,7-dimethylxanthine, 3'-deamino-3'-morpholino-13-deoxo-10-hydroxycaminomycin, 4-demethoxy-3-deamino-3-aziridinyl-4-methylsulphonyl-daunorubicin, 5-FU, 6-meracaptopurine, 6-thioguanine, 9-nitrocamptothecin, amrubicin, annamycin, antineoplaston, arsenic trioxide, asparaginase, azacitidine, bevacizumab, BCG live, benzylguanine, bexarotene, bisantrene, bleomycin, busulfan, cachectin, capecitabine, carboplatin, carmustine, chlorambucil, chloroquinoxaline, cis-aminedichloro(2-methylpyridine)platinum, cisplatin, cladribine, clofarabine, cloretazine, CPT-11, cyclophosphamide, cytarabine, dacarbazine, dactinomycin, daunomycin, decitabine, denileukin, depsipeptide, dexamethasone, dexifosfamide, diarizidinylspermine, dibromodulcitol, dibrospidium chloride, doxorubicin, elinafide, epirubicin, cetuximab, estramustine, ET-743, etoposide, exemestane, floxuridine, fludarabine, fotemustine, galarubicin, gemcitabine, gemtuzumab, glufosfamide, GPX100, heptaplatin, trastuzumab, hydroxyurea, ibritumomab, idarubicin, ifosfamide, imatinib mesylate, improsulfan tosylate, interferon, gefitinib, irinotecan, irofulven, lobaplatin, lomustine, lonidamine, mechlorethamine, melphalan, MEN 10755, methotrexate, mithramycin, mitomycin C, mitotane, mitoxantrone, nedaplatin, nimustine, novobiocin, oxaliplatin, pemetrexed, pentostatin, pinafide, pirarubicin, porfirimer, prednimustine, prednisolone, profiromycin, pumitepa, ranimustine, rebeccamycin, lenalidomide, rituximab, satraplatin, sertenef, streptozocin, erlinotib, tasonermin, taxanes such as taxol and taxotere, temozolomide, teniposide, thalidomide, thiotepa, tirapazimine, topotecan, tositumomab, trantuzumab, tretinoin, trofosfamide, troxacitabine, valrubicin, Vercyte, vinblastine, vincristine, vinorelbine, or zorubicin.

One embodiment provides a compound of formula (I) for use in medical therapy (including for use in treating solid tumors for which relatively few treatments are available).

Another embodiment provides for the use of a compound of formula (I) for the manufacture of a medicament for the treatment of a pathological condition or symptom in a mammal, such as a human, which is associated with cancer or tumor growth as described herein-above.

The subject can be any mammal having a susceptible cancer, i.e., a malignant cell population or tumor. The analogs are effective on human tumors in vivo as well as on human tumor cell lines in vitro.

One embodiment provides a method of using a compound of the invention to prepare a medicament effective to treat cancer with reduced toxicity compared to treatment with a substantially equally effective dose of irofulven (6-hydroxymethylacylfulvene). In on embodiment, the compound has the formula

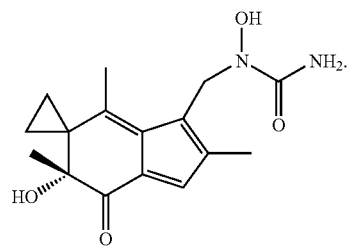

In one embodiment, the medicament is adapted for intravenous infusion. In another embodiment, the medicament is adapted for intraperitoneal or oral administration. In one embodiment, the medicament further comprises a second chemotherapeutic agent.

In one embodiment, the medicament is adapted to provide a dose of about 0.1 mg/kg to about 1.0 mg/kg of the compound. In another embodiment, the medicament is adapted to provide a dose of about 0.25 to about 0.65 mg/kg of the compound. In another embodiment, the medicament is formulated to provide a dose of less than 0.50 mg/kg of the compound. In one embodiment, the medicament is adapted to provide an effective dose of the compound by a dosing schedule of one dose per week for two weeks.

A method for decreasing a minimum effective or increasing the maximum tolerated anticancer dose of irofulven comprising replacing the 6-hydroxymethyl moiety of irofulven with $(CH_2)_n N(R^1)(OR^2)$, wherein
n is 1, 2, 3, 4, 5, or 6;
$R^1$ is $-C(X^1)X^2(R^9)$ or H;
$R^2$ is hydrogen, $-C(=O)(C_1\text{-}C_6)$alkyl, $-C(=O)(C_1\text{-}C_6)$alkyl$(C_6\text{-}C_{10})$aryl, $-C(=O)(C_6\text{-}C_{10})$aryl, or $-(C_1\text{-}C_6)$alkyl;

$X^1$ is O, or S;

$X^2$ is O, S, or $N(R^{10})$;

$R^9$ is hydrogen, $(C_1-C_6)$alkyl, $—(C_1-C_4)$alkyl$(C_6-C_{10})$aryl, or $—(C_6-C_{10})$aryl; or $—(C_1-C_4)$alkyl$(C_6-C_{10})$heteroaryl, or $—(C_6-C_{10})$heteroaryl;

$R^{10}$ is hydrogen or $(C_1-C_6)$alkyl; or a pharmaceutically acceptable salt thereof. In one embodiment, the 6-hydroxymethyl moiety of irofulven is replaced with $—CH_2N(OH)—C(=O)—NH_2$.

In one embodiment, the total dose (e.g., the total dose is the sum of single doses administered to a subject per cancer treatment (for example, if 0.4 mg/kg was administered once a week for two or three weeks, the total dose is 0.8 mg/kg or 1.2 mg/kg, respectively)) is at least about 40% less than would be required for irofulven. In another embodiment, the total dose is at least about 50% less than would be required for irofulven. In another embodiment, the total dose is at least about 60% less than would be required for irofulven.

In one embodiment, the cancer is a solid tumor, including, but not limited to, a lung, ovarian, prostate, breast, endometrial, bladder, renal, pancreatic, central nervous system, melanoma or colon carcinoma. In another embodiment, the cancer is a hematologic cancer, including, but not limited to, a B-cell leukemia, B-cell lymphoma, myeloma, T-cell leukemia, T-cell lymphoma, small cell leukemia, or small cell lymphoma. In one embodiment, the leukemia is acute lymphocytic leukemia (ALL) or chronic lymphocytic leukemia (CLL).

DETAILED DESCRIPTION

Figure 1:
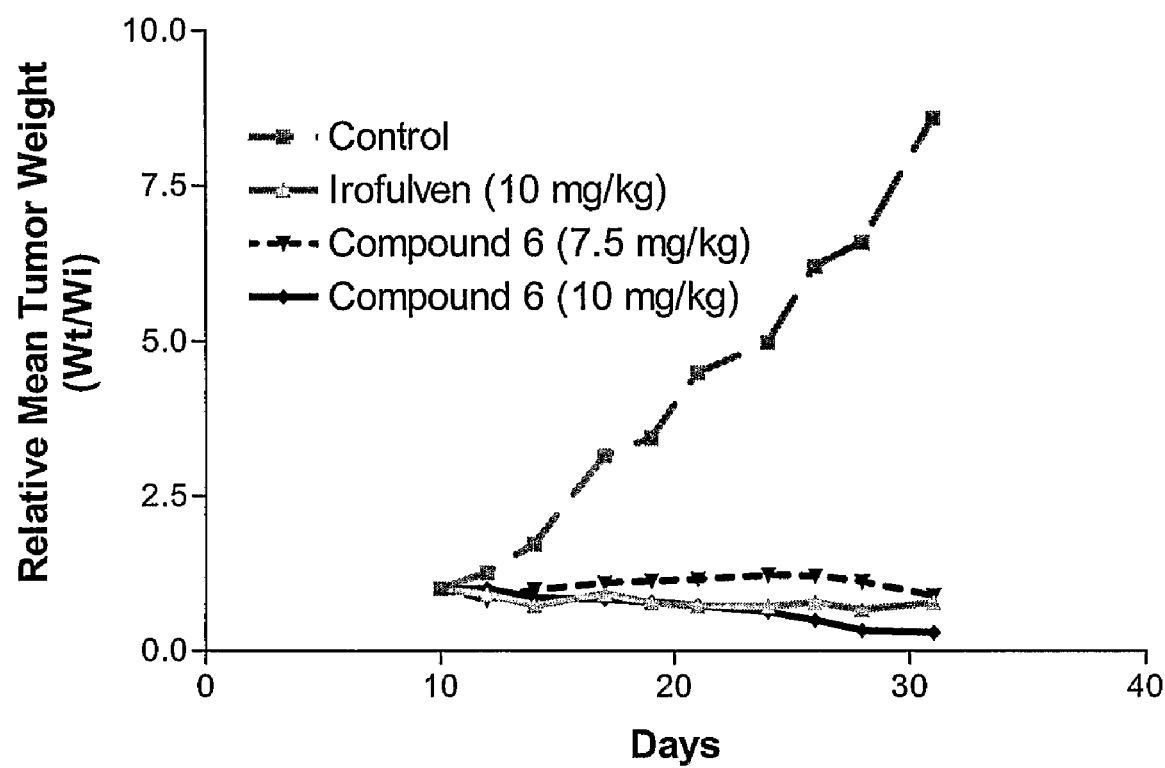
FIG. 1 is a graphic illustration of the Activity of compound 6 against the MV522 Xenograft Model.

One embodiment provides compounds of formula (I), and pharmaceutical compositions comprising a compound of formula (I), or a pharmaceutically acceptable salt thereof, in combination with a pharmaceutically acceptable diluent or carrier.

Another embodiment provides a therapeutic method to treat cancer, i.e., to inhibit tumor cell growth and/or kill cancer cells, in vitro or in vivo, by contacting such cells, such as by administration to a mammal, such as a human cancer patient, a therapeutically effective amount of a compound of formula (I), a pharmaceutically acceptable salt of the compound of formula (I), or a composition thereof, effective to inhibit the growth of said cancer cells, i.e., tumor cells. The present compounds may be particularly useful for the treatment of solid tumors for which relatively few treatments are available. Such tumors include lung, ovarian, prostate, breast, endometrial, bladder, renal, pancreatic, central nervous system, colon carcinomas, melanoma and the like. The present compounds can also be used against hematologic cancers (e.g., cancers of the blood and blood forming tissues), such as B-cell leukemia/lymphomas, myelomas, T-cell leukemia/lymphomas, and small cell leukemia/lymphomas. These leukemia/lymphomas could be either acute or chronic, for example, acute lymphocytic leukemia (ALL) or chronic lymphocytic leukemia (CLL).

Another embodiment provides a compound of formula (I) for use in medical therapy. In one embodiment, the medical therapy is the treatment of cancer (including the treatment of solid tumors and hematologic malignancies for which relatively few treatments are available). Non-limiting examples of such cancers include epidermoid and myeloid cancers, such as acute myelogenous leukemia (AML) or chronic myelogenous leukemia (CML), as well as lung, ovarian, breast and colon carcinomas. The present compounds can also be used in medical therapy against endometrial tumors, bladder cancer, pancreatic cancer, lymphoma, Hodgkin's disease, prostate cancer, sarcomas and testicular cancer as well as against tumors of the central nervous system, such as brain tumors, neuroblastomas and hematopoietic cell cancers such as B-cell leukemia/lymphomas, myelomas, T-cell leukemia/lymphomas, and small cell leukemia/lymphomas. These leukemia/lymphomas could be either acute or chronic, for example ALL or CLL.

One embodiment provides for the use of a compound of formula (I) for the manufacture of a medicament for the treatment of a pathological condition or symptom in a mammal, such as a human, which is associated with cancer or tumor growth as described herein.

The ability of a compound to inhibit cancerous growth and/or kill cancerous cells may be determined using pharmacological models which are well known to the art, or using the assays described herein.

As used herein, "treat," "treating" or "treatment" includes treating, reversing, preventing, ameliorating, or inhibiting cancer or a symptom of cancer.

As used herein, with respect to the present method, the term "inhibit" means either decreasing the cancer cell growth rate from the rate which would occur without treatment, or causing tumor cell mass to decrease in size. Inhibiting also includes causing a complete regression of the tumor or killing the cancerous cells. Thus, the present analogs can either be cytostatic or cytotoxic to the cancer cells.

As used herein, a "subject" is a vertebrate, preferably a mammal, more preferably a human. Mammals include, but are not limited to, humans, farm animals, sport animals and companion animals. Included in the term "animal" is dog, cat, fish, gerbil, guinea pig, hamster, horse, rabbit, swine, mouse, hamster, monkey (e.g., ape, gorilla, chimpanzee, orangutan), rat, sheep, goat, cow and bird.

The following definitions are used, unless otherwise described: halo is fluoro, chloro, bromo, or iodo. Alkyl denotes both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds described herein having a chiral center may exist in and be isolated in optically active and racemic forms. Some compounds may exhibit polymorphism. It is to be understood that the compounds described herein encompass any racemic, optically-active, polymorphic, or stereoisomeric form, or mixtures thereof, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anticancer activity using the standard tests described herein, or using other similar tests which are well known in the art.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Processes for preparing compounds of formula (I) or for preparing intermediates useful for preparing compounds of formula (I) are provided as further embodiments. Intermediates useful for preparing compounds of formula (I) are also provided as further embodiments.

Specific values listed below for radicals, substituents, and ranges, are for illustration only; they do not exclude other defined values or other values within defined ranges for the radicals and substituents.

A specific value for $X^1$ is O.
A specific value for $X^2$ is O or $N(R^{10})$.
Another specific value for $X^2$ is $N(R^{10})$.
Another specific value for $X^2$ is O.
A specific value for $R^1$ is —C(=O)OR$^9$, or —C(=O)N(R$^{10}$)(R$^9$), or H.
Another specific value for $R^1$ is —C(=O)OR$^9$.
Another specific value for $R^1$ is —C(=O)OCH$_2$CH$_3$.
Another specific value for $R^1$ is —C(=O)OCH$_2$Ph.
Another specific value for $R^1$ is —C(=O)OC(CH$_3$)$_3$.
Another specific value for $R^1$ is —C(=O)N(R$^{10}$)(R$^9$).
Another specific value for $R^1$ is —C(=O)N(R$^{10}$)CH$_2$CH$_3$.
Another specific value for $R^1$ is —C(=O)N(R$^{10}$)CH$_2$Ph.
Another specific value for $R^1$ is —C(=O)N(R$^{10}$)C(CH$_3$)$_3$.
Another specific value for $R^1$ is —C(=O)N(R$^{10}$)C(CH$_3$)$_3$.
A specific value for $R^2$ is hydrogen, —C(=O)(C$_1$-C$_6$)alkyl, —C(=O)(C$_1$-C$_6$)alkyl(C$_6$-C$_{10}$)aryl, or —(C$_1$-C$_6$)alkyl.
Another specific value for $R^2$ is hydrogen, —C(=O)(C$_1$-C$_4$)alkyl, or —C(=O)(C$_1$-C$_4$)alkyl(C$_6$-C$_{10}$)aryl.
Another specific value for $R^2$ is hydrogen, —C(=O)CH$_3$ (acetyl, Ac), —C(=O)CH$_2$CH$_3$, —C(=O)CH$_2$phenyl, —C(=O)CH$_2$CH$_2$phenyl, —CH$_3$, or —CH$_2$CH$_3$.
Another specific value for $R^2$ is hydrogen, —C(=O)CH$_3$, —C(=O)CH$_2$CH$_3$, —C(=O)CH$_2$phenyl, or —C(=O)CH$_2$CH$_2$phenyl.
Another specific value for $R^2$ is hydrogen, —C(=O)CH$_3$, or —C(=O)CH$_2$phenyl.

Another specific value for $R^2$ is hydrogen.
Another specific value for $R^2$ is —C(=O)CH$_3$.
Another specific value for $R^2$ is —C(=O)CH$_2$phenyl.
A specific value for $R^3$ is hydrogen, —CH$_3$, or —CH$_2$CH$_3$.
Another specific value for $R^3$ is —CH$_3$.
A specific value for $R^6$ is hydrogen, —CH$_3$, or —CH$_2$CH$_3$.
Another specific value for $R^6$ is —CH$_3$.
Another specific value for $R^7$ is —OH.
A specific value for $R^8$ is —CH$_3$, or —CH$_2$CH$_3$.
Another specific value for $R^8$ is —CH$_3$.
Another specific value for $R^9$ is hydrogen.
Another specific value for $R^9$ is —CH$_3$.
Another specific value for $R^9$ is —CH$_2$CH$_3$.
Another specific value for $R^9$ is —CH$_2$Ph.
Another specific value for $R^9$ is —C(CH$_3$)$_3$.
A specific value for $R^{10}$ is hydrogen or $(C_1-C_4)$alkyl.
Another specific value for $R^{10}$ is hydrogen, CH$_3$ or —CH$_2$CH$_3$.
Another specific value for $R^{10}$ is hydrogen or —CH$_3$.
Another specific value for $R^{10}$ is methyl.
Another specific value for $R^{10}$ is hydrogen.
A specific value for n is 1, 2, or 3.
Another specific value for n is 1, or 2.
Another specific value for n is 1.
Another specific value for n is 2.
Another specific value for n is 3.

In one embodiment, a specific group of compounds have the optional bond (—) present; $R^5$ absent; $R^3$, $R^6$ and $R^8$ are each —CH$_3$; $R^4$ is hydrogen; $R^7$ is —OH; and n is 1, 2, or 3.

In another embodiment, $R_6$ and $R_7$ together are ethylenedioxy, and $R^1$ is H; $R^2$ and $R^5$ are absent; $R^3$ and $R^4$ are H, and $R^8$ is CH$_3$.

Processes for preparing compounds of formula (I) are provided as further embodiments and are illustrated by the following procedures in which the meanings of the generic radicals are as given above unless otherwise qualified and is illustrated in Scheme 1 below.

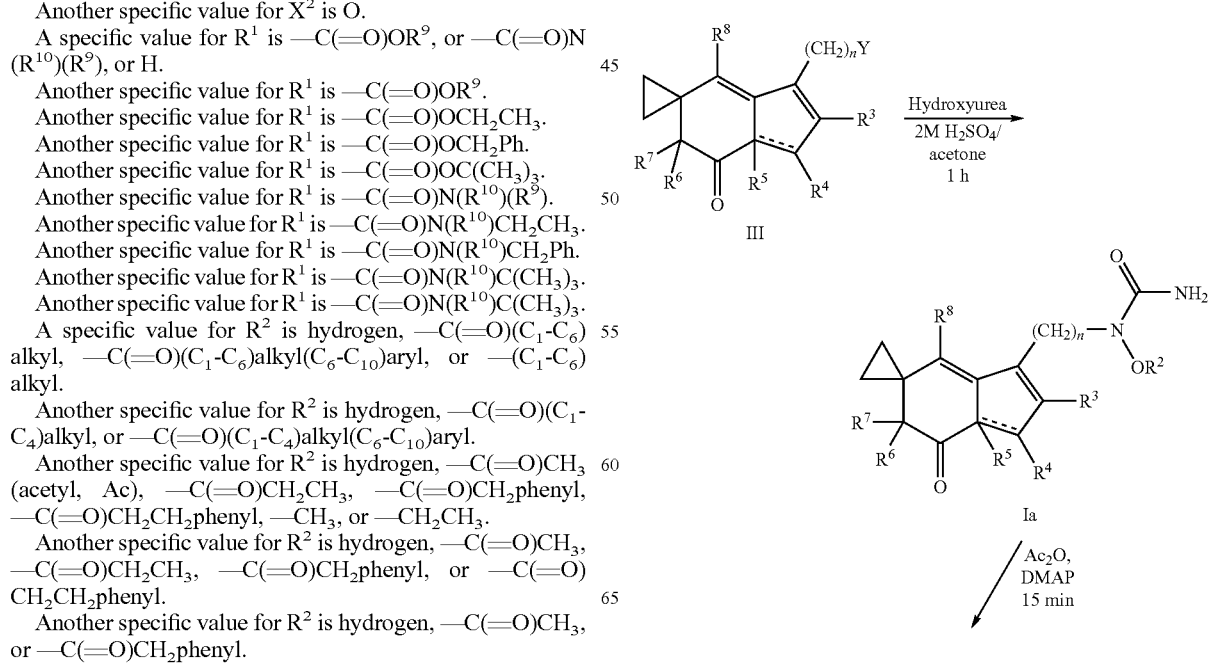

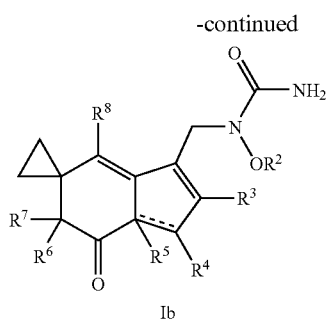

Ib

Precursors useful in preparing the compounds described herein may be derived from illudin S, 6-hydroxymethyl acylfulvene (HMAF, i.e., the compound of formula (III), for example where Y is —OH, n is 1, $R^3$ is $CH_3$, $R^4$ is H, $R^5$ is absent, $R^6$ is $CH_3$, $R^7$ is OH and $R^8$ is $CH_3$ and fulvene) the syntheses of which are known in the art (See e.g., WO 91/04754; WO 94/18151).

Specific compounds of formula (I) include but are not limited to:

6

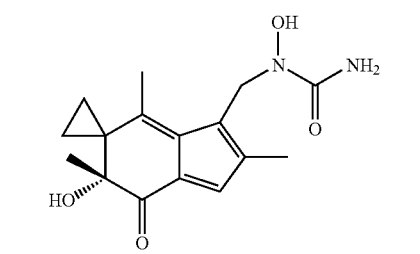

7

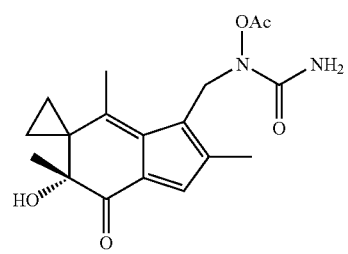

8

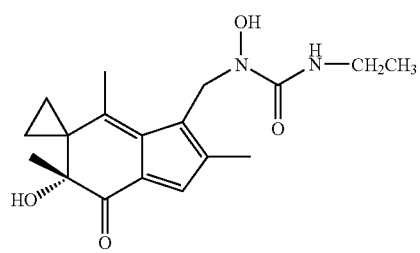

9

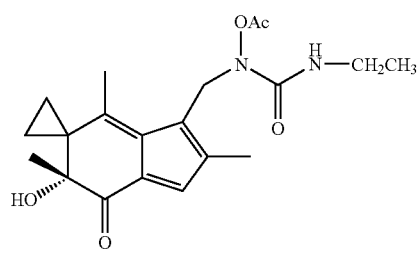

10

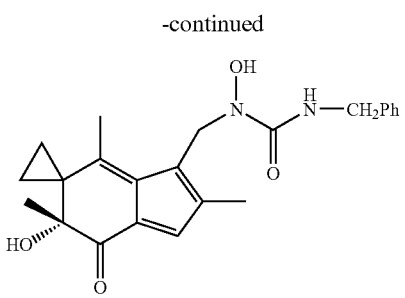

11

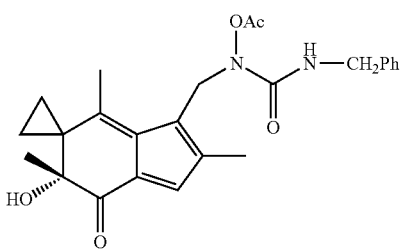

12

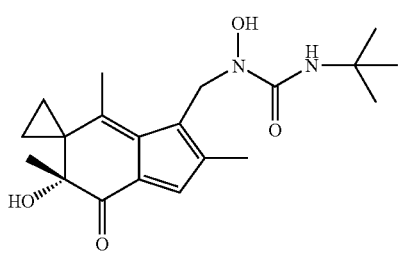

13

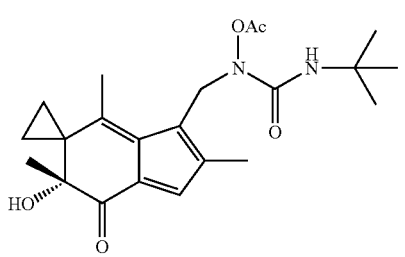

14

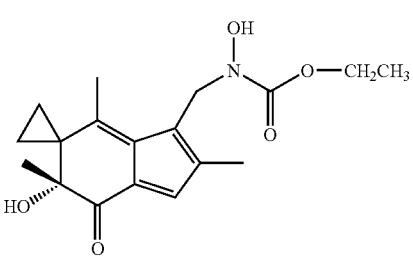

15

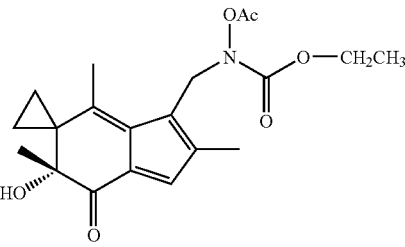

-continued

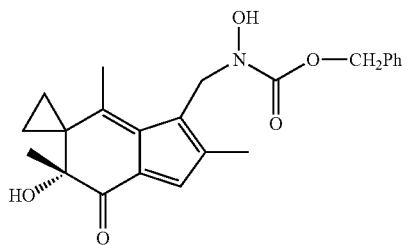
16

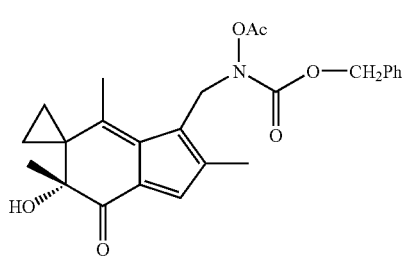
17

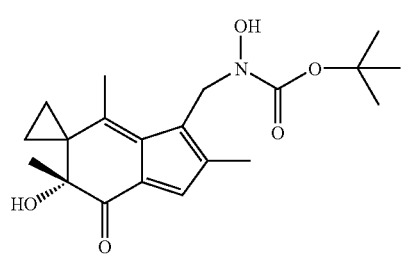
18

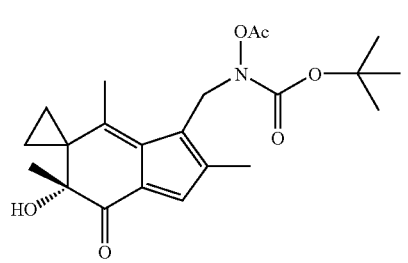
19

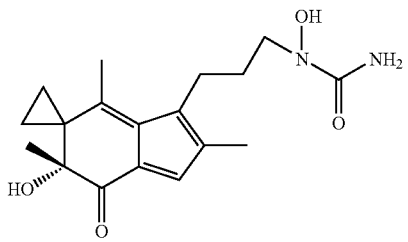
20

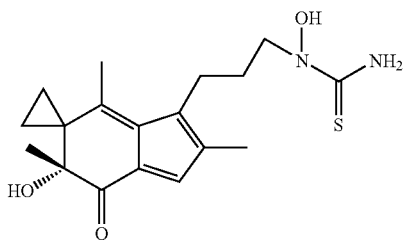
21

-continued

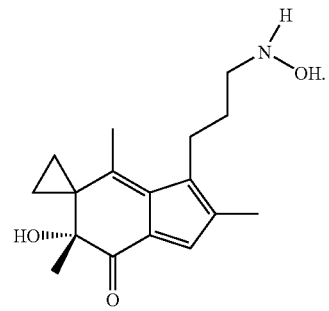
22

Conditions suitable for ester and amide preparation are well known to the art. For example, the conversions can be carried out under conditions similar to those described in the Examples.

Intermediates useful for preparing compounds of formula (I) include compounds having the formula:

These compounds can be prepared using methods known in the art. See, for example, U.S. Pat. No. 5,932,553 or U.S. Pat. No. 5,439,936.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula (I) can be formulated as pharmaceutical compositions and administered to a mammalian host, such as a human patient in a variety of forms adapted to the chosen route of administration, e.g., orally or parenterally, by intravenous, intramuscular, topical or subcutaneous routes, and the like.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. Isotonic agents can be included, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, examples of methods of preparation are vacuum drying and freeze drying, which yield a powder of the active ingredient plus any additional desired ingredient present in the previously sterile-filtered solutions.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula (I) can be determined by correlating their in vitro activity with in vivo activity in animal models, such as murine or dog models as taught for illudin analogs such as those of U.S. Pat. Nos. 5,439,936 and 5,523,490, to activity in higher mammals, such as children and adult humans as taught, e.g., in Borch et al. (U.S. Pat. No. 4,938,949).

Generally, the concentration of the compound(s) of formula (I) in a liquid composition, such as a lotion, will be from about 0.1-25 wt-%, such as from about 0.5-10 wt-%. The concentration in a semi-solid or solid composition such as a gel or a powder will be about 0.1-5 wt-%, such as about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attending physician or clinician.

In general, however, a suitable dose will be in the range of from about 0.5 to about 100 mg/kg, e.g., from about 10 to about 75 mg/kg of body weight per day, such as 5 to about 50 mg per kilogram body weight of the recipient per day, including in the range of 6 to 90 mg/kg/day, such as in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of about 0.5 to about 75 $\mu$M, such as, about 1 to 25 $\mu$M, including, about 2 to about 10 $\mu$M. This may be achieved, for example, by the intravenous injection of a 0.05 to 5% solution of the active ingredient, optionally in saline, or orally administered as a bolus containing about 1-500 mg of the active ingredient. Desirable blood levels may be maintained by continuous infusion to provide about 0.01-5.0 mg/kg/hr or by intermittent infusions containing about 0.4-15 mg/kg of the active ingredient(s).

The therapeutically effective amount of analog necessarily varies with the subject and the cancer to be treated. However, it has been found that relatively high doses of the analogs can be administered due to the decreased toxicity compared to illudin S and illudin M. A therapeutic amount between 30 to 112,000 µg per kg of body weight is especially effective for intravenous administration while 300 to 112,000 µg per kg of body weight is effective if administered intraperitoneally. As one skilled in the art would recognize, the amount, such as the minimum effective dose or the maximum tolerated dose can be varied depending on the method of administration and the type of cancer to be treated. For irofulven, effective doses, including minimum effective doses and maximum tolerated doses, are known to those of skill in the art and/or can be determined through routine experimentation.

Embodiments of the invention will be further described by reference to the following detailed examples.

EXAMPLES

Synthesis of Illudin Analogs

General Experimental Methods. Reactions were conducted under $N_2$ atmosphere in oven-dried glassware employing standard air-free manipulation techniques.

Synthesis of illudin S, 1, hydroxymethylacylfulvene (HMAF, 3) and fulvene are known in the art (See, e.g., U.S. Pat. Nos. 5,523,490, 5,439,942, 5,439,936, 5,563,176, 5,723,632, 5,856,580, and 5,932,553).

Reaction solvents were dried and distilled prior to use. Methylene chloride ($CH_2Cl_2$) was distilled from $CaH_2$ under $N_2$. All other reagents and solvents were used as received from commercial sources. Solvents were removed under reduced pressure using a rotary evaporator.

All chromatography was carried out with silica gel. Analytical TLC was carried out on silica gel plates. Reactions were routinely monitored by TLC.

$^1$H-NMR and $^{13}$C-NMR spectra were measured at 400 and 100 MHz, respectively.

Example 1

N-hydroxy-N-(methylacylfulvene)urea (6)

To a solution of irofulven (200 mg, 0.812 mmol) in a 1:1 mixture (8.0 mL) of acetone and 2M $H_2SO_4$ was added hydroxyurea (125 mg, 1.64 mmol). The mixture was stirred for 1 h at room temperature then partitioned between ethyl acetate and water. The organic extract was washed with saturated $NaHCO_3$ and brine then dried with $MgSO_4$ and concentrated. The crude product was chromatographed (1:3 hexanes-ethyl acetate) to give 206 mg of the title compound (83%) as an orange gum: $^1$H-NMR (CDCl$_3$) δ 0.70 (m, 1H), 1.07 (m, 1H), 1.36 (m, 1H), 1.36 (s, 3H), 1.48 (m, 1H), 2.08 (s, 3H), 2.17 (s, 3H), 4.57 (d, J=14.8 Hz, 1H), 4.80 (d, J=14.8 Hz, 1H), 5.37 (br, 2H), 7.07 (s, 1H) $^{13}$C-NMR (CDCl$_3$) δ 10.0, 13.7, 14.7, 16.8, 27.9, 37.9, 46.0, 76.3, 126.4, 128.9, 135.1, 138.5, 144.6, 160.8, 162.1, 198.2; HRMS for $C_{16}H_{21}N_2O_4$ (MH$^+$) calcd 305.1501. Found 305.1505; UV $\lambda_{max}$ (EtOH) 332 nm (ε6621).

Example 2

N-Acetoxy-N-(methylacylfulvene)urea (7)

To a solution of 6 (20.4 mg, 67.0 µmol) and Ac$_2$O (7.0 µL, 74 µmol) in CH$_2$Cl$_2$ (2.0 mL) was added DMAP (2.0 mg, 16 µmol). The mixture was stirred for 15 min then added directly to a silica gel column and chromatographed (10:1 hexanes-ethyl acetate) to give 23.2 mg of 6(quant.) as an orange gum: $^1$H-NMR (CDCl$_3$) δ $^1$H-NMR (CDCl$_3$) δ 0.71 (m, 1H), 1.06 (m, 1H), 1.35 (m, 1H), 1.36 (s, 3H), 1.46 (m, 1H), 1.91 (s, 3H), 2.10 (s, 3H), 2.13 (s, 3H), 3.90 (br s, 1H), 4.77 (br, 2H), 5.25 (s, 2H), 7.04 (s, 1H); $^{13}$C-NMR (CDCl$_3$) δ 9.7, 13.2, 14.5, 17.0, 18.3, 27.6, 38.0, 46.1, 76.4, 126.4, 127.1, 133.5, 138.5, 144.0, 159.5, 161.7, 167.6, 198.0; HRMS for $C_{18}H_{22}N_2O_5$ calcd 346.1529. found 346.1519; UV $\lambda_{max}$ (EtOH) 332 nm (ε6673).

Example 3

Anti-Cancer Activity of Acylfulvene Analogs in vitro

The anti-cancer activities of compounds 6, 7, 14, 16, 18, 20, 21 and 22 were compared to that of irofulven, 3, using MV522 lung cancer cells in vitro (See Kelner M. J. et al., Cancer Res. 1987, 47, 3186). At 2 hours exposure time, compound 6 and 22 had activity comparable to irofulven whereas the acetylated derivative 7 was more potent than irofulven (Table 1). Analogs 14, 16, 18, 20, and 21 were less potent against the MV522 cells in comparison to irofulven at the two hour time point. After 48 hour incubations, the potency rank order of the acylfulvenes were irofulven>7, 22>20>6>14>21>16>18.

TABLE 1

Anticancer Activity of Acylfulvene Analogs against the MV522 Tumor Cell Line after 2 Hour and 48 Hour Exposures

| | $IC_{50}$ (nM)$^a$ | |
| --- | --- | --- |
| Compound | 2 h | 48 h |
| 6 | 800 ± 300 | 210 ± 20 |
| 7 | 90 ± 10 | 130 ± 10 |
| 14 | 3200 ± 300 | 350 ± 80 |
| 16 | 3000 ± 500 | 1100 ± 400 |
| 18 | 3500 ± 400 | 2200 ± 400 |
| 20 | 1600 ± 400 | 150 ± 10 |
| 21 | 3400 ± 1000 | 440 ± 90 |
| 22 | 700 ± 100 | 130 ± 40 |
| irofulven | 1200 ± 100 | 70 ± 10 |

$^a$IC$_{50}$ is the concentration of the acylfulvene at which 50% inhibition occurred in the thymidine incorporation into cellular DNA (2 hour) and Trypan blue (48 hour) assay Using four different cell lines, HT29 colon, OVCAR-3 ovarian, AsPC-1 pancreatic, and PC-3 prostate carcinoma, the IC$_{50}$ values of compound 6 and irofulven were established for one hour incubations using the MTS viability assay (Buttke T. M. et al., J Immunol Methods. 1993, 157, 233). Compared to irofulven, compound 6 had similar potency against the ovarian, colon and prostate cell lines; however, it had greater potency against the pancreatic cell line (Table 2).

TABLE 2

Anti-Cancer Activity of Compound 6 and Irofulven Against a Panel of Cancer Cell Lines after 1 Hour Exposure

| Cell Line | Compound 6 GI50 (µg/mL) | Irofulven GI50 (µg/mL) |
| --- | --- | --- |
| HT29 | 0.68 | 1.4 |
| OVCAR-3 | 0.6 | 0.15 |
| AsPC-1 | 16 | >100 |
| PC-3 | 0.41 | 0.58 |

GI50 measures the growth inhibitory power of the test agent

Example 4

Anti-Cancer Activity of Acylfulvene Analogs in vivo

Figure 2:
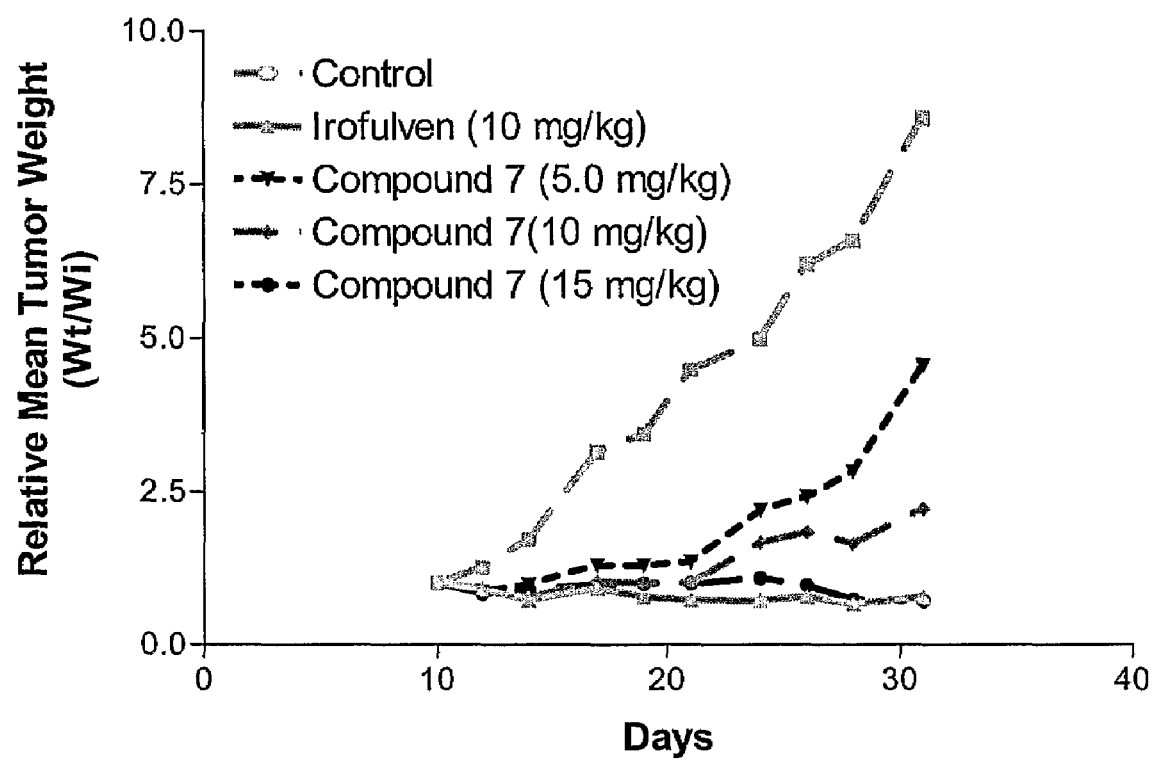
FIG. 2 is a graphic illustration of the Activity of compound 7 on a 3/wk for 21 d administration schedule against the MV522 Xenograft Model.

The MV522 xenograft model was used to test the in vivo activity of compounds 6 and 7 as previously described (Kelner M. J. et al., *Invest New Drugs*. 1996, 14, 161). Mice bearing subcutaneous MV522 tumors were dosed intraperitoneally three times a week for three weeks (3/wk for 21 d) at 10 mg/kg of irofulven, doses ranging from 7.5 to 10 mg/kg for compound 6, or 5 to 15 mg/kg for compound 7 (FIGS. 1 and 2 and Table 3). Compound 6 had potent anti-tumor activity against MV522 tumors, producing 4/6 and 5/5 partial responses in mice treated with 7.5 and 10 mg/kg doses, respectively. Partial responses (4/6) were observed in the mice receiving 15 mg/kg of compound 7; whereas, tumor growth inhibition was produced in the 5 and 10 mg/kg groups (56 and 79%, respectively). Based on final relative tumor weight, compounds 6 and 7 had similar anti-tumor potency compared to irofulven. The results of these biological studies suggest that compounds 6 and 7 are effective agents for human anti-tumor therapy.

TABLE 3

Anti-Tumor Activity of Acylfulvenes in the MV522 Mouse Xenograft Model

| Group | N | Dose (mg/kg) | Route & Schedule | Relative Mean Tumor Weight (Wt/Wi) | % Tumor Growth Inhibition | PR |
|---|---|---|---|---|---|---|
| Control | 8 | — | i.p., 3/wk for 21 d | 8.6 | — | — |
| Irofulven | 8 | 10 | i.p., 3/wk for 21 d | 0.8 | 100% | 6/7 |
| Compound 6 | 6 | 7.5 | i.p., 3/wk for 21 d | 0.9 | 100% | 4/6 |
| Compound 6 | 5 | 10 | i.p., 3/wk for 21 d | 0.3 | 100% | 5/5 |
| Compound 7 | 6 | 5 | i.p., 3/wk for 21 d | 4.5 | 56% | — |
| Compound 7 | 6 | 10 | i.p., 3/wk for 21 d | 2.2 | 79% | — |
| Compound 7 | 6 | 15 | i.p., 3/wk for 21 d | 0.7 | 100% | 4/6 |

N, Number mice per group; i.p., intraperitoneal, 3/wk; three times per week; d, day; Wt, tumor weight on last study day; Wi, tumor weight on first dosing day; % Tumor growth inhibition is calculated using the formula: $100 - ((\Delta \text{Tumor Weight Treated}/\Delta \text{Tumor Weight Control}) \times 100)$; PR, Partial Response (defined as less than tumor weight at the start of the study).

Example 5

Plasma Stability of Acylfulvene Analogs In Vitro

Figure 3:
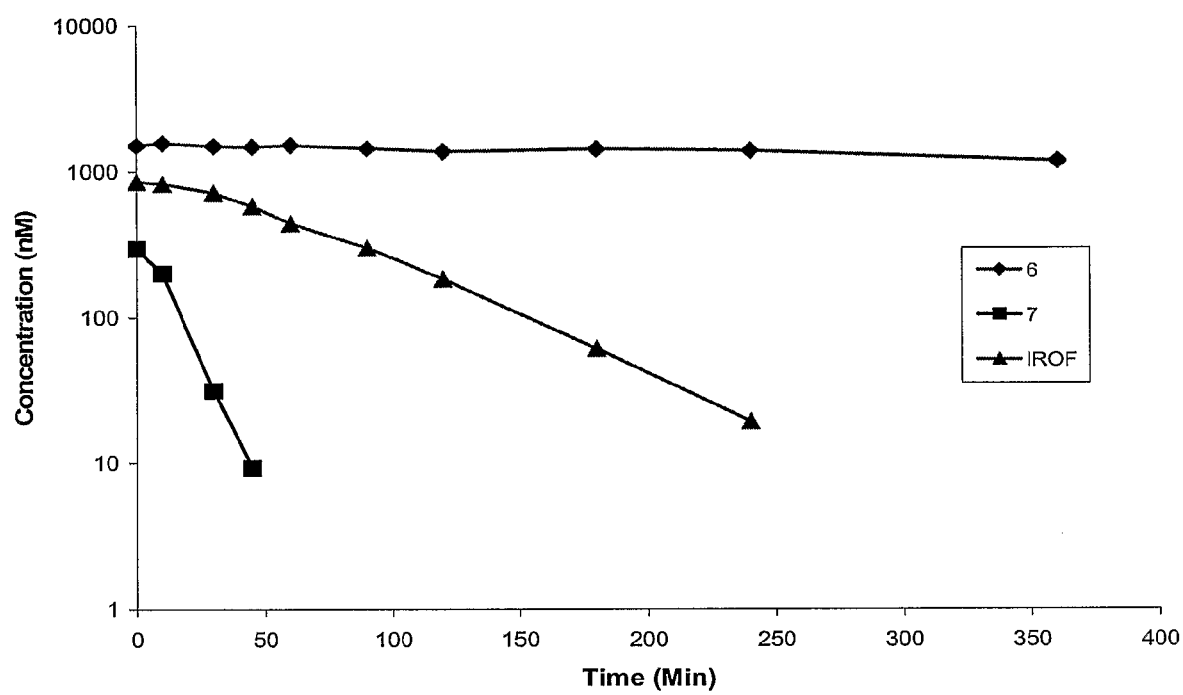
FIG. 3 is a graphic illustration of the stability of irofulven and compounds 6 and 7 in human plasma at 37° C.

Compounds 6 and 7 were compared against irofulven for their respective plasma stability (e.g., the enhanced stability or in vivo terminal phase elimination half life (T½) of a compound in plasma; it is believed that the greater the stability and T½ the more likely it is that the compound will be incorporated into or have an effect on a cancerous cell, such as cells of a tumor or a hematologic cancerous cell). Pooled fresh human plasma was spiked with each analog, and the compound stability profile was measured at 37° C. using LC/MS/MS. Compound 6 was more stable and Compound 7 was less stable in human plasma than irofulven (FIG. 3). These properties differentiate Compounds 6 and 7 from irofulven and may have enhanced therapeutic potential. The increased plasma stability of Compound 6 may be particularly advantageous in drug formulation and delivery as it relates to increased exposure of the tumor to the drug. Thus, compound 6 has increased stability in human plasma in vitro (FIG. 3).

Example 6

Pharmacokinetics of Acylfulvene Analogs

Figure 4:
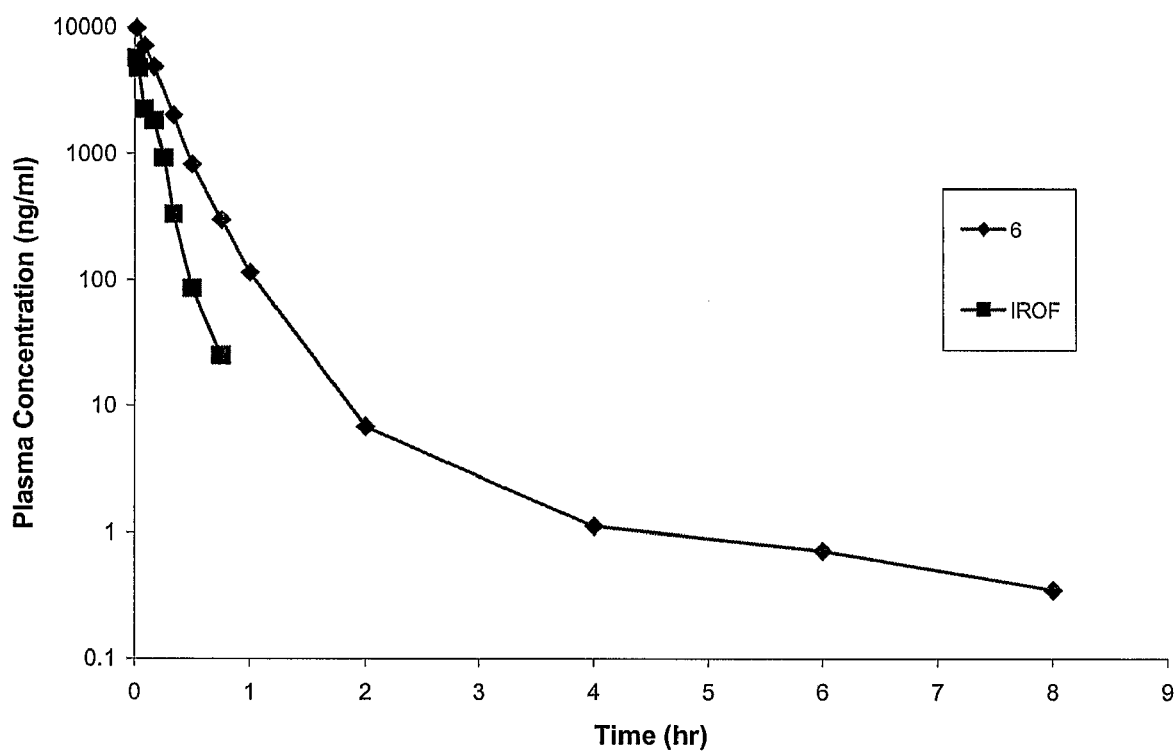
FIG. 4 is a graphic illustration of the plasma-time concentration profiles for irofulven and compound 6 following 5 mg/kg IV administration in the mouse.

The pharmacokinetics (PK) of Compound 6 was investigated in the CD-1 male mouse. A single intravenous administration of 5 mg/kg was followed by sequential blood collections and analysis of plasma by LC/MS/MS. Compared with irofulven, Compound 6 demonstrated different PK characteristics (FIG. 4 and Table 4). The $C_{max}$ and AUC were greater and the T½ was significantly longer for Compound 6, and total body clearance (CLp) and volume of distribution at steady state (Vdss) were reduced for Compound 6 compared with irofulven. Thus, compound 6 has a pharmacokinetic profile that is significantly different from irofulven (FIG. 4; Table 4).

TABLE 4

Pharmacokinetics of Compound 6 Compared to Irofulven following a Single Intravenous Administration of 5 mg/kg Compound 6 or Irofulven in Male CD-1 Mice

| Analog | Dose (mg/kg) | Cmax (ng/ml) | AUC (0-t) (ng · hr/ml) | AUC(0-∞) (ng · hr/ml) | $T_{1/2}$ (hr) | CLp (ml/hr/kg) | Vdss (ml/kg) |
|---|---|---|---|---|---|---|---|
| 6 | 5 | 9730 | 2200 | 2200 | 2.36 | 2270 | 548 |
| Irofulven | 5* | 5650 | 691 | 695 | 0.0988 | 7200 | 948 |

*Irofulven concentrations extrapolated from a 12.9 mg/kg IV dose

Example 7

Novel Dosing Schedule for Acylfulvene Analogs

Figure 5:
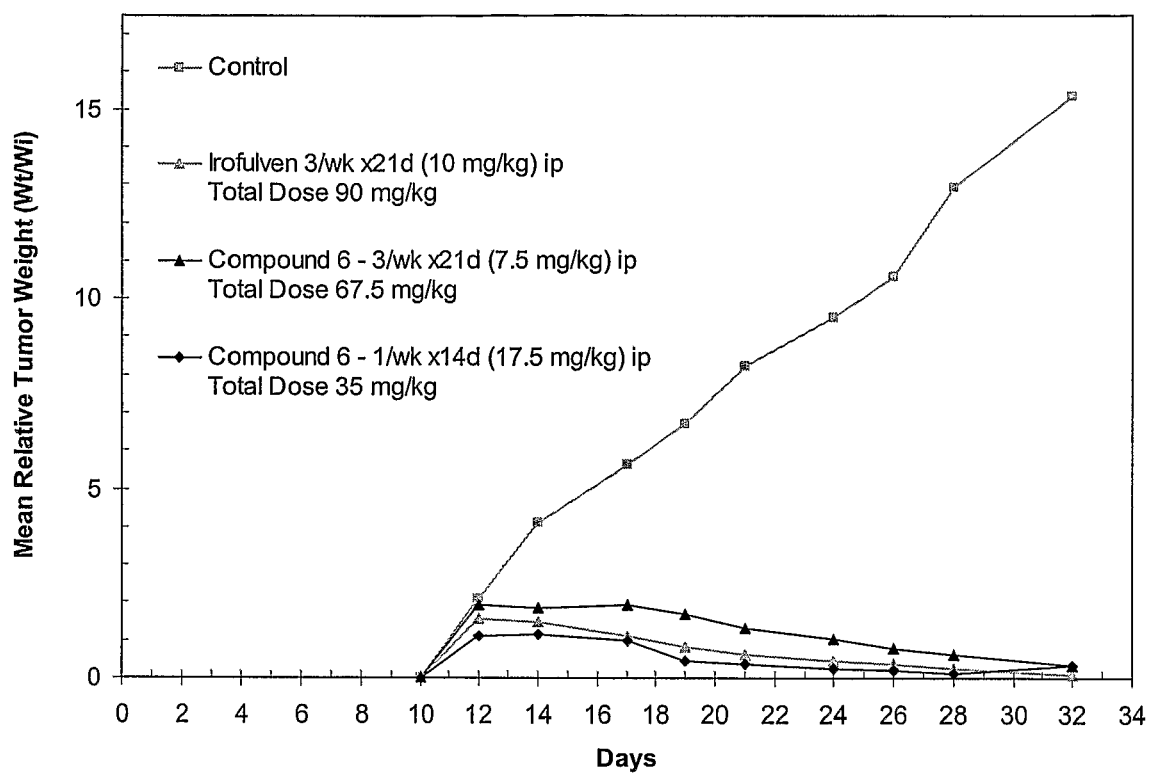
FIG. 5 is a graphic illustration of the activity of Compound 6 on a 3/wk for 21 d and 1/wk for 14 d administration schedule against the MV522 tumor cell line in the nude mouse Xenograft model.

A novel dosing schedule for acyfulvene analogs is described herein. This dosing schedule requires less frequent administration of individual dosages exceeding the previously-determined maximum tolerated dose (MTD) for each dose on an intermittent schedule of 3/wk for 21 d. For example, compound 6 was tested on a dosing schedule of 1/wk for 14 d. On this schedule, the total cumulative dose was less than the total cumulative dose administered on the 3/wk for 21 d-schedule, but with equal efficacy (FIG. 5). The 3/wk for 21 d dosing schedule is a standard method of administration for irofulven. The 1/wk for 21 d schedule for Compound 6 disclosed herein was unexpected based on prior work and presents a unique opportunity to administer less total dose of a cytotoxic chemotherapeutic less frequently and thereby reduce the overall toxic effect on the patient. This represents an increase in human safety and compliance, as a weekly dosing schedule is easier to follow than a more frequent dosing schedule.

The MV522 xenograft model was used to test the in vivo activity of Compound 6 administration on a weekly schedule. Nude mice bearing subcutaneous MV522 tumors were dosed intraperitoneally (IP) 1/wk for 14 d at 17.5 mg/kg Compound 6 vs 7.5 mg/kg Compound 6 or 10 mg/kg irofulven on the intermittent schedule (3/wk for 21 d). The comparator dosages were the previously-determined efficacious MTDs for the 3/wk for 21 d schedule (FIG. 5). The data showed that Compound 6 on the weekly schedule had similar anti-tumor activity compared to the comparator controls on the intermittent schedule despite a lower total dose. The results suggest that the compounds disclosed herein, including but not limited to, Compound 6, using an administration regimen novel for the acylfulvenes, are particularly useful as a safer therapeutic method for treating cancer in humans.

Thus, the compounds of the invention provide for one to use less drug less frequently. Additionally, the compounds of the invention allow for better efficacy at the same dose as irofulven or the substantially similar efficacy at a lower dose than irofulven. An effective single dose (which could be administered multiple times during a week (e.g., 2, 3 or more times per week) for several weeks (e.g., one, two, three or more weeks) or once a week for one, two three or more weeks) includes about 0.1 to about 1.0 mg/kg; about 0.2 to about 0.8 mg/kg, about 0.3 to about 0.7 mg/kg, about 0.4 to about 0.6 mg/kg, or about 0.5 mg/kg. For example, an effective single dose includes less than about 0.5 mg/kg, less than about 0.45 mg/kg, less than about 0.4 mg/kg, less than about 0.35 mg/kg, less than about 0.30 mg/kg, less than about 0.25 mg/kg, less than about 0.2 mg/kg, or less than about 0.15 mg/kg. In one embodiment, a single dose is given once a week for two weeks.

For example, one embodiment provides a therapeutic method comprising administering to a subject in need of cancer treatment a compound of the following formula:

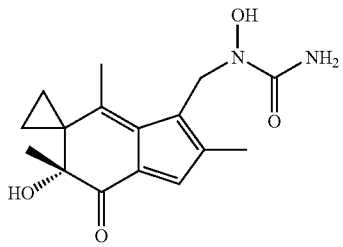

or a pharmaceutically acceptable salt thereof; at a dose sufficient to decrease or reverse the progression of said cancer, wherein said administered dose is lower than the dose of irofulven necessary to achieve a therapeutically substantially equivalent decrease or reversal of cancer progression, wherein said cancer is a lung, ovarian, colon, prostate, or pancreatic cancer.

Another embodiment provides a therapeutic method comprising administering to a subject in need of cancer treatment a compound of the following formula:

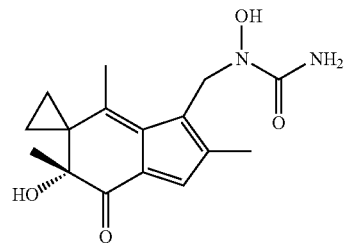

or a pharmaceutically acceptable salt thereof, wherein said compound is administered by intravenous infusion at a dose of less than 0.45 mg/kg, wherein said cancer is a lung, ovarian, colon, prostate, hepatocellular, or pancreatic cancer. In one embodiment, the compound is administered at a dose of less than 0.4 mg/kg. In another embodiment, a chemotherapeutic agent is co-administered to the subject (e.g., cancer patient).

Another embodiment provides a therapeutic method comprising administering to a subject in need of cancer treatment a compound of the following formula:

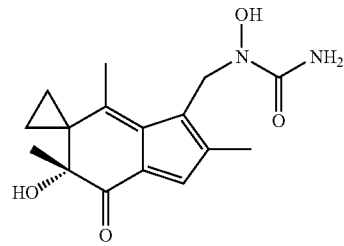

or a pharmaceutically acceptable salt thereof, wherein said compound is administered by intravenous infusion at a dose of less than 11 mg/m$^2$.

Another embodiment provides a therapeutic method comprising repeatedly administering to a patient in need of cancer treatment a compound of the following formula:

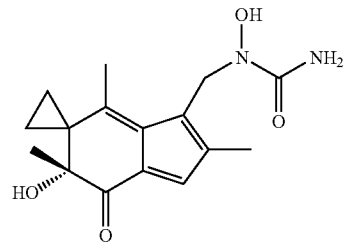

or a pharmaceutically acceptable salt thereof, in an amount and at a frequency sufficient to decrease or reverse the progression of said cancer, wherein said frequency is lower than the frequency necessary to achieve a therapeutically equivalent decrease or reversal of cancer progression by repeated administration of irofulven, wherein said cancer is a lung, colon, prostate, or pancreatic cancer.

All publications, patents, and patent documents are incorporated by reference herein, as though individually incorporated by reference. The invention has been described with reference to various specific embodiments and techniques. However, it should be understood that many variations and modifications may be made while remaining within the spirit and scope of the invention.

What is claimed is:

1. A compound having formula (I)

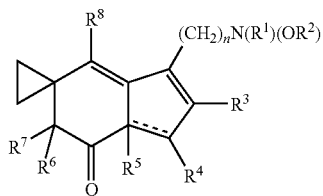

wherein
$R^1$ is —C(X$^1$)X$^2$(R$^9$) or H; X$^1$ is O, or S; X$^2$ is O, S, or N(R$^{10}$);
$R^2$ is hydrogen, —C(=O)(C$_1$-C$_6$)alkyl, —C(=O)(C$_1$-C$_6$)alkyl(C$_6$-C$_{10}$)aryl, —C(=O)(C$_6$-C$_{10}$)aryl, or —(C$_1$-C$_6$)alkyl;
$R^3$ is hydrogen, or (C$_1$-C$_6$)alkyl;
$R^4$ is hydrogen, —SCH$_2$CO$_2$(C$_1$-C$_6$)alkyl, —O—(C$_6$-C$_{10}$)aryl, or —S—(C$_6$-C$_{10}$)aryl; where aryl is optionally substituted with halo, OH or (C$_1$-C$_4$)alkyl;
$R^5$ is hydrogen, OH, or absent;
$R^6$ is hydrogen, or (C$_1$-C$_6$)alkyl; and
$R^7$ is OH or Si((C$_1$-C$_4$)alkyl)$_3$; or
$R^6$ and $R^7$ together are ethylenedioxy;
$R^8$ is (C$_1$-C$_6$)alkyl; optionally substituted with OH or halo;
$R^9$ is hydrogen, (C$_1$-C$_6$)alkyl, —(C$_1$-C$_4$)alkyl(C$_6$-C$_{10}$)aryl, or —(C$_6$-C$_{10}$)aryl; or —(C$_1$-C$_4$)alkyl(C$_6$-C$_{10}$)heteroaryl, or —(C$_6$-C$_{10}$)heteroaryl;
$R^{10}$ is hydrogen or (C$_1$-C$_6$)alkyl; n is 1, 2, 3, 4, 5, or 6; and the bond represented by — is optionally present or absent; or
pharmaceutically acceptable salts thereof.

2. The compound of claim 1, wherein $R^1$ is —C(=O)OR$^9$, or —C(=O)N(R$^{10}$)(R$^9$).
3. The compound of claim 1, wherein $R^1$ is —C(=O)OR$^9$.
4. The compound of claim 3, wherein $R^1$ is —C(=O)OCH$_2$CH$_3$.
5. The compound of claim 3, wherein $R^1$ is —C(=O)OCH$_2$Ph.
6. The compound of claim 3, wherein $R^1$ is —C(=O)OC(CH$_3$)$_3$.
7. The compound of claim 1, wherein $R^1$ is —C(=O)N(R$^{10}$)(R$^9$).
8. The compound of claim 7, wherein $R^1$ is —C(=O)N(R$^{10}$)CH$_2$CH$_3$.
9. The compound of claim 7, wherein $R^1$ is —C(=O)N(R$^{10}$)CH$_2$Ph.
10. The compound of claim 7, wherein $R^1$ is —C(=O)N(R$^{10}$)C(CH$_3$)$_3$.
11. The compound of claim 7, where $R^{10}$ is hydrogen or (C$_1$-C$_4$)alkyl.
12. The compound of claim 7, where $R^{10}$ is hydrogen, methyl or ethyl.
13. The compound of claim 7, where $R^{10}$ is hydrogen or methyl.
14. The compound of claim 7, where $R^{10}$ is methyl.
15. The compound of claim 7, where $R^{10}$ is hydrogen.
16. The compound of claim 1, wherein $R^2$ is hydrogen, —C(=O)(C$_1$-C$_6$)alkyl, —C(=O)(C$_1$-C$_6$)alkyl(C$_6$-C$_{10}$)aryl, or —(C$_1$-C$_6$)alkyl.
17. The compound of claim 1, wherein $R^2$ is hydrogen, —C(=O)(C$_1$-C$_6$)alkyl, or —C(=O)(C$_1$-C$_6$)alkyl(C$_6$-C$_{10}$)aryl.
18. The compound of claim 1, wherein $R^2$ is hydrogen, —C(=O)(C$_1$-C$_4$)alkyl, —C(=O)(C$_1$-C$_4$)alkyl(C$_6$-C$_{10}$)aryl, or —(C$_1$-C$_4$)alkyl.
19. The compound of claim 1, wherein $R^2$ is hydrogen, —C(=O)CH$_3$, —C(=O)CH$_2$CH$_3$, —C(=O)CH$_2$phenyl, —C(=O)CH$_2$CH$_2$phenyl, —CH$_3$, or —CH$_2$CH$_3$.
20. The compound of claim 1, wherein $R^2$ is hydrogen, —C(=O)CH$_3$, —C(=O)CH$_2$CH$_3$, —C(=O)CH$_2$phenyl, or —C(=O)CH$_2$CH$_2$phenyl.
21. The compound of claim 1, wherein $R^2$ is hydrogen, —C(=O)CH$_3$, or —C(=O)CH$_2$phenyl.
22. The compound of claim 1, wherein $R^2$ is hydrogen.
23. The compound of claim 1, wherein $R^2$ is —C(=O)CH$_3$.
24. The compound of claim 1, wherein $R^2$ is —C(=O)CH$_2$phenyl.
25. The compound of claim 1, wherein $R^3$ is hydrogen, —CH$_3$, or —CH$_2$CH$_3$.
26. The compound of claim 1, wherein $R^3$ is —CH$_3$.
27. The compound of claim 1, wherein $R^6$ is hydrogen, —CH$_3$, or —CH$_2$CH$_3$.
28. The compound of claim 1, wherein $R^6$ is —CH$_3$.
29. The compound of claim 1, wherein n is 1, 2, or 3.
30. The compound of claim 1, wherein n is 1.
31. The compound of claim 1, wherein n is 2.
32. The compound of claim 1, wherein n is 3.
33. The compound of claim 1, wherein the optional bond (—) is present; $R^5$ is absent; $R_3$, $R_6$ and $R_8$ are each —CH$_3$; $R_4$ is H; $R_7$ is OH; and n is 1.
34. The compound of claim 1, having the formula:

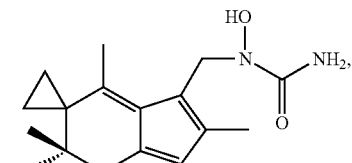

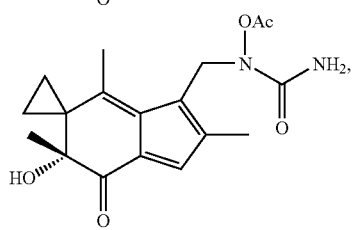

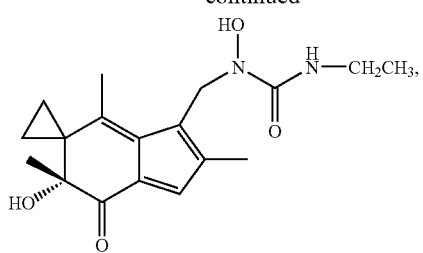
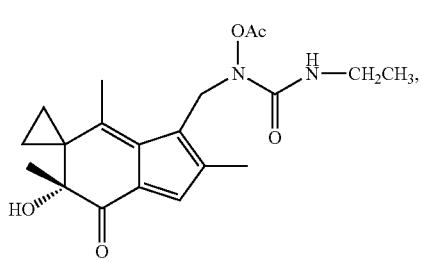
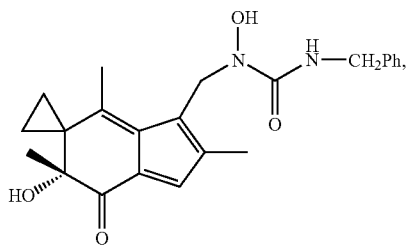
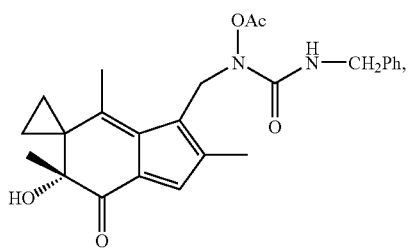
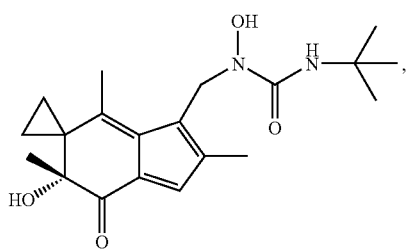
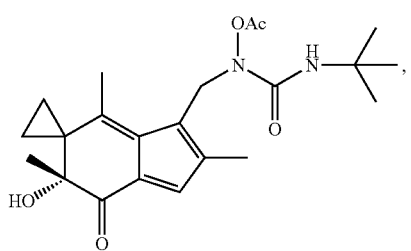
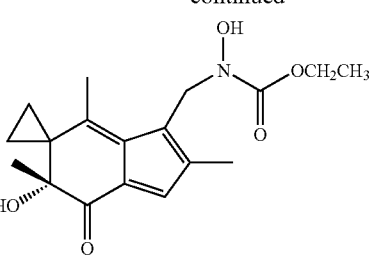
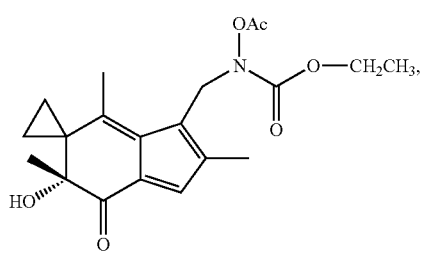
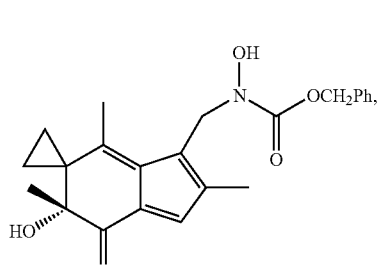
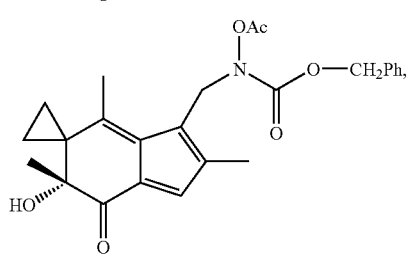
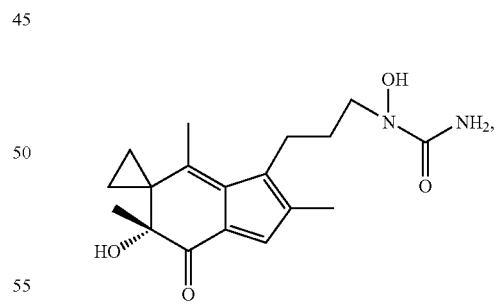
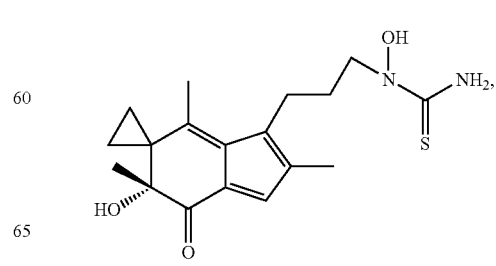

-continued

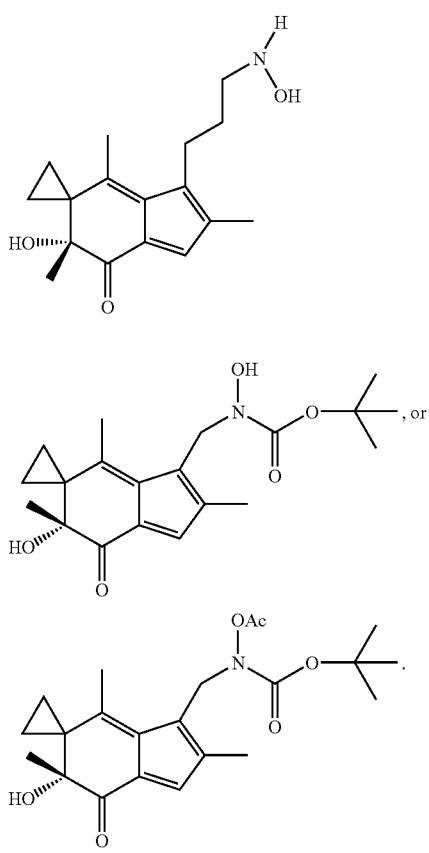

a pharmaceutically acceptable salt thereof.

35. The compound of claim 34, having the formula

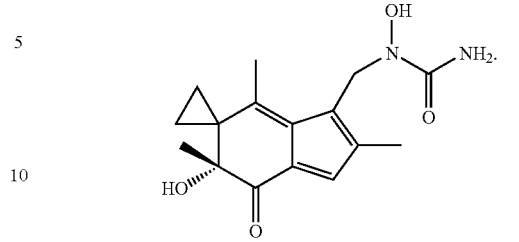

or a pharmaceutically acceptable salt thereof.

36. A therapeutic method of inhibiting cancer cell growth in a subject in need of such therapy comprising administering a therapeutic amount of the compound of claim 1.

37. The therapeutic method of claim 36 wherein the subject is a human cancer patient.

38. The therapeutic method of claim 36 wherein the patient is afflicted with a solid tumor.

39. The therapeutic method of claim 38 wherein the solid tumor is a lung, ovarian, prostate, breast, endometrial, bladder, renal, pancreatic, central nervous system, melanoma or colon carcinoma.

40. The therapeutic method of claim 36 wherein the patient is afflicted with a hematologic cancer.

41. The therapeutic method of claim 40 wherein the hematologic cancer is a B-cell leukemia, B-cell lymphoma, myeloma, T-cell leukemia, T-cell lymphoma, small cell leukemia, or small cell lymphoma.

42. The therapeutic method of claim 41 wherein leukemia is acute lymphocytic leukemia (ALL) or chronic lymphocytic leukemia (CLL).

* * * * *

UNITED STATES PATENT AND TRADEMARK OFFICE
CERTIFICATE OF CORRECTION

PATENT NO. : 7,655,695 B2  Page 1 of 1
APPLICATION NO. : 11/997432
DATED : February 2, 2010
INVENTOR(S) : Trevor C. McMorris et al.

It is certified that error appears in the above-identified patent and that said Letters Patent is hereby corrected as shown below:

In column 15, line 59, delete "Found" and insert -- found --, therefor.

In column 25, lines 15-20, in Claim 34, after " 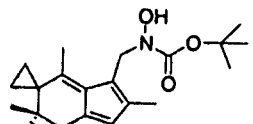 " delete "or".

In column 25, lines 25-30, in Claim 34, after " 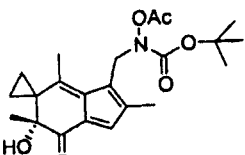 " delete "." and insert -- , or --, therefor.

Signed and Sealed this

Twenty-seventh Day of April, 2010

David J. Kappos
*Director of the United States Patent and Trademark Office*